US008939903B2

(12) United States Patent  
Roberts et al.

(10) Patent No.: US 8,939,903 B2  
(45) Date of Patent: Jan. 27, 2015

(54) MEASUREMENT OF EMOTIONAL RESPONSE TO SENSORY STIMULI

(75) Inventors: Kenneth George Roberts, Melbourne (AU); Elaine Wong, Melbourne (AU)

(73) Assignee: Forethough Pty Ltd, Melbourne (AU)

( * ) Notice: Subject to any disclaimer, the term of this patent is extended or adjusted under 35 U.S.C. 154(b) by 378 days.

(21) Appl. No.: 13/162,820

(22) Filed: Jun. 17, 2011

(65) Prior Publication Data

US 2012/0035428 A1  Feb. 9, 2012

Related U.S. Application Data

(60) Provisional application No. 61/355,741, filed on Jun. 17, 2010.

(51) Int. Cl.
*G06F 19/00* (2011.01)
*A61B 5/16* (2006.01)
(Continued)

(52) U.S. Cl.
CPC .............. *A61B 5/165* (2013.01); *G06N 3/004* (2013.01); *G06F 19/3443* (2013.01); *G06N 3/006* (2013.01); *G06F 19/363* (2013.01); *A61B 5/744* (2013.01)
USPC ......... 600/300; 705/7.11; 705/7.29; 705/7.32

(58) Field of Classification Search
None
See application file for complete search history.

(56) References Cited

U.S. PATENT DOCUMENTS 4,931,934 A * 6/1990 Snyder .......................... 434/236
5,676,138 A   10/1997 Zawilinski
(Continued)

FOREIGN PATENT DOCUMENTS

WO   WO 2004/070502 A2   8/2004
WO   WO 2005/116871 A1   12/2005

OTHER PUBLICATIONS

Penn, David. "Getting Animated About Emotion." ESOMAR Congress Paper, Montreal. Sep. 2008.*
(Continued)

*Primary Examiner* — William Thomson
*Assistant Examiner* — Davin Sands
(74) *Attorney, Agent, or Firm* — Dorsey & Whitney LLP

(57) ABSTRACT

A method of measuring emotional response of at least one subject to a specific sensory stimulus comprises establishing (202) a plurality of basic emotions for measurement, including one or more positive affect emotions and one or more negative affect emotions. The subject is presented (302) with the specific sensory stimulus, and for each basic emotion is further presented (306) with a computer-generated display comprising interactive animated visual images representative of a metaphorical concept corresponding with the basic emotion. Input is then received (308) from the subject, who is enabled to adapt the animated visual images to accord with an emotional response to the sensory stimulus. The received input is converted to a corresponding quantitative emotional response value for each basic emotion. The quantitative emotional response value may be a difference value derived from a change in emotional state of the subject and based upon an initial calibration of emotional state performed prior to presenting the subject with the sensory stimulus. A visual presentation (1000) is generated, which comprises representations (1004, 1012, 1014) of the quantitative emotional response values for each of the plurality of basic emotions, whereby the relative emotional response of the subject in respect of each basic emotion is visually distinguishable.

24 Claims, 15 Drawing Sheets

(51) Int. Cl.
*G06N 3/00* (2006.01)
*A61B 5/00* (2006.01)

(56) References Cited

U.S. PATENT DOCUMENTS

| | | | | |
|---|---|---|---|---|
| 6,160,540 | A * | 12/2000 | Fishkin et al. | 345/184 |
| 8,160,918 | B1 * | 4/2012 | Blair et al. | 705/7.32 |
| 8,239,000 | B1 * | 8/2012 | Morris et al. | 600/410 |
| 2005/0209909 | A1 | 9/2005 | Dull et al. | |
| 2007/0066916 | A1 * | 3/2007 | Lemos | 600/558 |
| 2007/0203426 | A1 | 8/2007 | Kover et al. | |
| 2007/0265507 | A1 * | 11/2007 | de Lemos | 600/300 |
| 2008/0010108 | A1 | 1/2008 | Roberts et al. | |
| 2008/0065468 | A1 * | 3/2008 | Berg et al. | 705/10 |
| 2008/0205692 | A1 * | 8/2008 | Hinkle et al. | 382/100 |
| 2010/0221687 | A1 * | 9/2010 | Forbes | 434/236 |

OTHER PUBLICATIONS

Desmet, Pieter. "Measuring emotion: Development and application of an instrument to measure emotional responses to products." Funology. Springer Netherlands, 2005. 111-123.*

Bargh, John A. "Losing Consciousness: Automatic Influences on Consumer Judgment, Behavior, and Motivation" Journal of Consumer Research, 2002; vol. 29, 280-285.

Chartrand, Tanya L. "The Role of Conscious Awareness in Consumer Behavior" J. of Consumer Psychology 15(3), 2005 203-210.

Greenwald et al. "Measuring Individual Differences in Implicit Cognition: The Implicit Association Test" Journal of Personality and Social Psychology 1998, vol. 74, No. 6, 1464-1480.

Kövecses Zoltán, "Metaphor and Emotion: Language, Culture, and Body in Human Feeling" Cambridge University Press. 2003. Cover Page, Table of Contents, pp. 5, 9, 23, 30, 51, 60, 89, 93, 103, 109, 111, 116, 129, 130, 134, 170, 174, 175, 176, and 198.

Laros et al. "Emotions in consumer behavior: a hierarchical approach" J. of Business Research 58 (2005) 1437-1445.

Penn, David. "Metaphors Matter" 20 pages Apr. 2008 Conquest Research and Consultancy. London, UK www.conquestuk.com.

Richins, Marsha L. "Measuring Emotions in the Consumption Experience" Journal of Consumer Research, vol. 24. Sep. 1997. pp. 127-146.

Slingerland, Edward G. Conceptual blending, somatic marking, and normativity: a case example from ancient Chinese *Cognitive Linguistics 16-3* (2005), 557-584.

Barry, Ann Marie. "Visual Intelligence: perception, image and manipulation in visual communication." State University of New York. 1997. Cover page and Table of Contents 5 pages.

Tellis, Gerard J. Advertising and Sales Promotion Strategy. Cover page and Table of Contents, and Chapter 5, pp. 118-135.

Penn, David. "Beyond Neuroscience: Engagement and Metaphor." ESOMAR 2007. 16 pages (2007).

Penn, David. "Neuromania, the New Irrationalism and Why we need to Rehumanise research." Conquest Research & Consultancy Ltd. Mar. 2012. 10 pages.

Penn, David. "Contagion—Making Sense of a New Marketing Epidemic." Conquest Research & Consultancy Ltd., Mar. 22, 2010. 36 pages.

Buzzell, Robert D. et al. "Market share—a key to profitability: An ongoing study of 57 companies reveals a link between ROI and market share—the bigger the better." Harvard Business Review, Jan.-Feb. 1975. pp. 97-106.

Gaeth, Gary J. et al. "Designing Managed Care Dental Benefit Plans: An application of choice-based conjoint analysis." Marketing Health Services, Winter/Spring 2000. pp. 39-44 (2000).

Geurtz, Michael D. et al. "Forecasting Market Share." The Journal of Business Forecasting, Winter 1992-1993. pp. 17-22 (1993).

Inquisit 3 Feature List, www.millisecond.com, Sep. 8, 2008.

Inquisit homepage, www.millisecond.com, Jan. 22, 2009.

What's New in Inquisit 3, www.millisecond.com, Apr. 22, 2009.

Metaphorix homepage, www.metaphorixuk.com, Apr. 20, 2012.

About Metaphorix: Want to know more about the theory and ideas behind Metaphorix?, www.metaphorixuk.com, Apr. 22, 2012. 3 pages.

Metaphorix Papers, www.metaphorixuk.com, Jul. 15, 2012.

"Conjoint Analysis Part I: Developing New Products," forethought Research, The Science of Marketing. www.forethought.com.au (2009).

"Conjoint Analysis Part II: Optimum Pricing," forethought Research, The Science of Marketing. www.forethought.com.au (2009).

* cited by examiner

During this questionnaire you will be using a character to represent you for certain questions. Please choose your gender.

700

Please pick the character from below who you want to represent you for this quetionnaire

701

708

710

712

MEASUREMENT OF EMOTIONAL RESPONSE TO SENSORY STIMULI

PRIORITY CLAIM

This application claims priority to U.S. Provisional Application No. 61/355,741, filed Jun. 17, 2010, the content of which is hereby incorporated in its entirety by reference.

FIELD OF THE INVENTION

The present invention relates generally to the field of research relating to emotional responses of human beings, and more particularly to methods and apparatus for assessing emotional state of an individual responsive to specific sensory stimuli.

BACKGROUND OF THE INVENTION

Advances in the study of neurology and clinical psychology have led to advances in the methods and tools used to assess and analyse emotional responses of individuals to various sensory stimuli. According to Ann Marie Barry, in her book 'Visual Intelligence: Perception, Image, and Manipulation in Visual Communication' (State University of New York: 1997), up until the mid-1980s it was widely believed that sensory information was first processed via conscious and unconscious thought, prior to the generation of an emotional response, for example via the autonomic nervous systems and the endocrine system. The most extreme proponents of this view argued that cognitive appraisal was a necessary precondition for emotional reaction.

However, from about the mid-1980s the neurobiologist Joseph LeDoux, and others, conducted various experiments mapping the operations of the so-called 'limbic system' in greater detail. This research indicated that, although emotional functions might be mediated by other brain regions, the amygdala (a subcortical region buried deep within the temporal lobe) strongly determines our emotional response to sensory stimuli. In Barry's words, the amygdala acts 'as a sentry to ready the body in response to danger' and 'attaches emotional significance to incoming data and readies the body to act in intense situations by signalling the hypothalamus to secrete hormones, initiating a fight-or-flight response. It alerts the autonomic nervous system and prepares the muscles for movement; and it warns the brainstem to secrete chemicals that heighten alertness and reactivity in key areas of the brain. All of this can occur independently of a conscious decision to act.'

As a consequence of the work of LeDoux, and many others since, the broad consensus is now that much of cognition is no more than a post-response rationalisation for the emotions resulting from the effect of sensory stimuli on the limbic system. LeDoux has hypothesised that this may explain our general inability to fully understand the origins and operations of our emotions, since the cortical systems responsible for understanding only become involved after the fact.

One outcome of this neurological research is an appreciation that human beings' emotional responses to sensory stimuli cannot be effectively measured through mechanisms, such as questionnaires, which necessarily require high-level cognitive processing. Accordingly, neuroscientific research has resulted in the development of various techniques to measure unconscious emotional responses. This is possible because, as the foregoing discussion indicates, emotions necessarily involve a physiological component, which is susceptible to measurement. Various physiological variables have been used to measure changes in emotions, including galvanic skin response (GSR), blood pressure, heart rate and respiration. It is no coincidence that such readily measured variables are also commonly used by so-called 'lie detector', or polygraph, apparatus, the basis of which is identification of telltale emotional responses to the expression of untruths. More-sophisticated measurement techniques include electromyography (EMG), electrocardiography (ECG), electroencephalography (EEG) and functional magnetic resonance imaging (fMRI). All of these physiological techniques have in common an ability to identify the presence of an emotional response, often in real-time, but little or no capacity to differentiate between different types of emotional response. An unidentified emotional response is nothing more than arousal (e.g. of the limbic system), from which little might be concluded, particularly since there may be no differentiation between quite distinct emotions (e.g. love and hate).

In the field of cognitive linguistics it has been noted that metaphors appear able to evoke an emotional response directly, without cognitive processing. (Slingerland, E. D., 'Conceptual Blending, Somatic Marking and Normativity,' *Cognitive Linguistics*, Volume 16 No. 3, 2005, pages 557 to 564; Kovecses, Z., 'Metaphor and Emotion—Language, Culture, and Body in Human Feeling,' Cambridge University Press, UK: 2000.) The process of acquiring and exercising such metaphorical connections is called 'conflation', whereby individuals acquire some common metaphors automatically and unconsciously via the process of neural learning, and through experience.

As a result of these discoveries and observations, it has been proposed that animated visual metaphors, rather than verbal questioning, may provide a more-effective mechanism to measure emotional response. An early attempt to harness this idea is the Metaphorix™ system, developed by Conquest Research and Consultancy Ltd (www.metaphorixuk.com). Trials of this system have demonstrated a loose correlation (Pearson Correlation Coefficient of 0.78) between emotional response as measured via Metaphorix scales, and success in the marketplace of products associated with corresponding brands. (Penn, D, 'Metaphors Matter,' *ARF Conference*, New York, April 2008.) However, these trials demonstrated only that a higher level of consumer engagement with a brand (measured as emotional response to the brand) is correlated with a higher market share. This result seems unsurprising, and furthermore provides no information as to cause and effect, nor is it able to explain the many outliers that defy the general trend.

It is therefore apparent that a need remains to provide improved methods for measuring emotional response of individuals to sensory stimuli. While such methods may find application within the field of market research (i.e. as with the Metaphorix™ system), effective tests for emotional response may have many other applications, for example in the fields of clinical psychology and neurology.

SUMMARY OF THE INVENTION

In one aspect the present invention provides a method of measuring emotional response of at least one subject to a specific sensory stimulus, comprising the steps of:
  establishing a plurality of basic emotions for measurement, including one or more positive affect emotions and one or more negative affect emotions;
  presenting the subject with the sensory stimulus;
  for each basic emotion, presenting the subject with a computer-generated display comprising interactive animated visual images representative of a metaphorical concept corresponding with the basic emotion;

receiving input from the subject whereby the subject is enabled to adapt the animated visual images to accord with an emotional response to the sensory stimulus;

converting the received input to a corresponding quantitative emotional response value for each basic emotion; and generating a visual presentation comprising representations of the quantitative emotional response values for all of the plurality of basic emotions, whereby the relative emotional response of the subject in respect of each basic emotion is visually distinguishable.

Advantageously, embodiments of the invention are thereby able to distinguish the subject's response in respect of a distinct plurality of different emotions, and to present these in a manner enabling subsequent evaluation of emotional responses, and not only to measure general levels of emotional arousal, as in more-limited prior art approaches.

In embodiments of the invention, the method may further comprise, prior to presenting the subject with the sensory stimulus, performing a calibration of an initial emotional state of the subject in respect of each basic emotion, and the step of converting the received input to a corresponding quantitative emotional response value determining a difference value for each basic emotion based upon a change in emotional state of the subject from the initial emotional state.

The calibration may comprise the steps of (without first presenting the subject with any sensory stimulus):

for each basic emotion, presenting the subject with the computer-generated display comprising interactive animated visual images representative of a metaphorical concept corresponding with the basic emotion; and receiving input from the subject whereby the subject is enabled to adapt the animated visual images to accord with a current emotional state of the subject.

Advantageously, performing an initial calibration procedure enables the differing initial emotional states of test subjects to be substantially factored out of the measurement.

Determining a difference value may comprise subtracting initial emotional-state values from corresponding values associated with the input received in response to the sensory stimulus. In alternative embodiments, other measures of change in emotional state may be employed.

In one embodiment, the plurality of basic emotions comprises positive affect emotions selected from the group: love; pride; contentment; and happiness. Further, the plurality of basic emotions comprises negative affect emotions selected from the group: anger; sadness; shame; and anxiety.

Also in an embodiment, the plurality of basic emotions further includes one or more neutral affect emotions. In one embodiment, a neutral affect emotion comprises surprise.

Animated visual images corresponding with each basic emotion may be established by a method comprising the steps of:

identifying a plurality of candidate metaphorical concepts and associated visual images;

testing each candidate image with a panel of test subjects to determine a strength of association of the image with the basic emotion;

selecting the candidate image with the strongest association with the basic emotion; and developing a computer-implemented sequence of animated interactive visual images representative of the metaphorical concept associated with the selected candidate image.

It will therefore be appreciated that the methodology for developing the computer-generated displays of interactive animated visual images has an objective and scientific basis.

It may be desirable that, prior to or during the step of receiving input, the subject is presented with a reminder of the sensory stimulus. Advantageously, this may refresh the subject's memory of the sensory stimulus, along with the corresponding emotional response. In some embodiments, the sensory stimulus comprises an audiovisual presentation, and one application involves the measurement of emotional response to advertisements and other audiovisual communications. The reminder may comprise a still image or a short sequence excerpted from the audiovisual presentation.

In some embodiments, the interactive animated visual images comprise an avatar representing the subject, which the subject manipulates to position the avatar both literally and metaphorically closer to, or further from, a position representative of a strong emotional response. The quantitative emotional response value may be a numerical value corresponding with the avatar position input by the subject on a scale from most distant to least distant from the position representative of the strong emotional response. In one embodiment, the quantitative emotional response value takes one of a plurality of discrete values, for example one of five, seven, nine or, in embodiments disclosed herein, 11 discrete values.

The visual presentation may comprise a numerical presentation, such as a table, list, spreadsheet or the like. Alternatively, or additionally, the visual presentation may comprise a graphical presentation, such as a graph (e.g. in polar or rectangular coordinates), a bar chart, a pie chart, or similar representation. Furthermore, the official presentation may comprise any combination of the foregoing numerical and/or graphical options.

In many applications of the invention the at least one subject will comprise a plurality of subjects. In this case, the corresponding quantitative emotional value for each basic emotion may be a single value derived from the combined input of all subjects. For example, the step of converting the received input to a corresponding quantitative emotional response value may comprise calculating an average response value for each basic emotion. However, other values may be of interest, for example a variance value may be computed in order to compare responses to different sensory stimuli across a range of test subjects.

In another aspect, the invention provides a method of comparing the emotional response of at least one subject to one or more specific sensory stimuli with a desired emotional response, including the steps of:

establishing a plurality of basic emotions for measurement, including one or more positive affect emotions and one or more negative affect emotions;

determining desired relative emotional response values for each of the plurality of basic emotions;

presenting the subject with a first sensory stimulus;

for each basic emotion, presenting the subject with a computer-generated display comprising interactive animated visual images representative of metaphorical concept corresponding with the basic emotion;

receiving input from the subject whereby the subject is enabled to adapt the animated visual images to accord with an emotional response to the sensory stimulus;

converting the received input to a corresponding quantitative emotional response value for each basic emotion; and generating a visual presentation comprising comparative representations of the quantitative emotional response values of the subject or all of the plurality of basic emotions, along with the corresponding desired emotional response values, whereby the correlation between the relative emotional response of the subject in respect of each basic emotion and the corresponding desired emotional response is visually distinguishable.

The subject, or plurality of subjects, may subsequently be presented with one or more further sensory stimuli, and steps (d) to (g) repeated for each said sensory stimulus. The plurality of sensory stimuli may be predetermined prior to any presentation to the subject or subjects, or may be developed in response to each presentation and emotional response measurement. For example, a sensory stimulus may be adaptively modified to improve the correlation between measured quantitative emotional response values and the predetermined desired emotional response values.

In some embodiments, the method may further include selecting one of the plurality of specific sensory stimuli on the basis of correlation between measured quantitative emotional response values and the desired emotional response values.

In yet another aspect, the invention provides a computer-implemented system for measuring the emotional response of at least one subject to a specific sensory stimulus, the system comprising:

at least one microprocessor;
at least one memory device, operatively coupled to the microprocessor; and
at least one input/output peripheral interface, operatively coupled to the microprocessor,
wherein the memory device contains executable instruction code which, when executed by the microprocessor, causes the system to implement a method comprising the steps of:
for each one of a plurality of basic emotions, including one or more positive affect emotions and one or more negative affect emotions, presenting the subject via the peripheral interface with a computer-generated display comprising interactive animated visual images representative of a metaphorical concept corresponding with the basic emotion;
receiving input from the subject via the peripheral interface whereby the subject is enabled to adapt the animated visual images to accord with an emotional response to a sensory stimulus previously presented to the subject;
converting the received input to a corresponding quantitative emotional response value for each basic emotion; and
generating a visual presentation comprising representations of the quantitative emotional response values for all of the plurality of basic emotions, whereby the relative emotional response of the subject in respect of each basic emotion is visually distinguishable.

In one embodiment, input from subjects is obtained via a web-based implementation, and the input/output peripheral interface thus includes a network interface providing connectivity to the Internet. In alternative embodiments, the system may comprise a stand-alone computing platform with appropriate programming, and the peripheral interface may include conventional user input/output devices, such as a display device, keyboard and pointing device (e.g. mouse).

Further features and advantages of the present invention will be apparent to those skilled in the art from the following description of embodiments of the invention, which should not be considered to be limiting of the scope of the invention as defined in any of the preceding statements, or in the claims appended hereto.

It is intended that, except where otherwise apparent from the context, the terms comprises/comprising and grammatical variations thereof when used in this specification indicate the presence of stated features, integers, steps or components or groups thereof, but do not preclude the presence or addition of one or more other features, integers, steps, components or groups thereof.

BRIEF DESCRIPTION OF THE DRAWINGS

Embodiments of the invention will now be described with reference to the accompanying drawings, in which.

DETAILED DESCRIPTION

Recent advances in neuroscience have revealed a great deal about the operation of the human mind. It is now widely accepted and understood that emotions guide and bias our decision-making, to a greater degree than the cognitive counterpart. Emotion is, in fact, the first response to any stimulus. It is therefore apparent that understanding and measuring emotional response is likely to have increasing application across a wide range of human endeavours, including, though not limited to, neurological and psychological investigations and research. Indeed, one early application for the measurement of emotional response to sensory stimuli lies within the field of market research. In particular, it is well-established that the relationship between consumers and brands can be highly emotional in nature, and that emotional responses to advertising presentations may be a better predictor of effectiveness than commonly used 'high attention'-based metrics, such as brand awareness and recall.

In addition, the large number of potential test subjects (i.e. all consumers) makes the marketing arena ideal for the development of new methodologies and systems for measuring emotional response. Accordingly, embodiments of the present invention are presented in this particular context, however it will be appreciated that the scope of the invention is in no way limited to this exemplary application. The methods and apparatus described herein are widely applicable to other contexts in which it is desired to measure the emotional responses of individuals, or representative population samples, to selected sensory stimuli.

Figure 1:
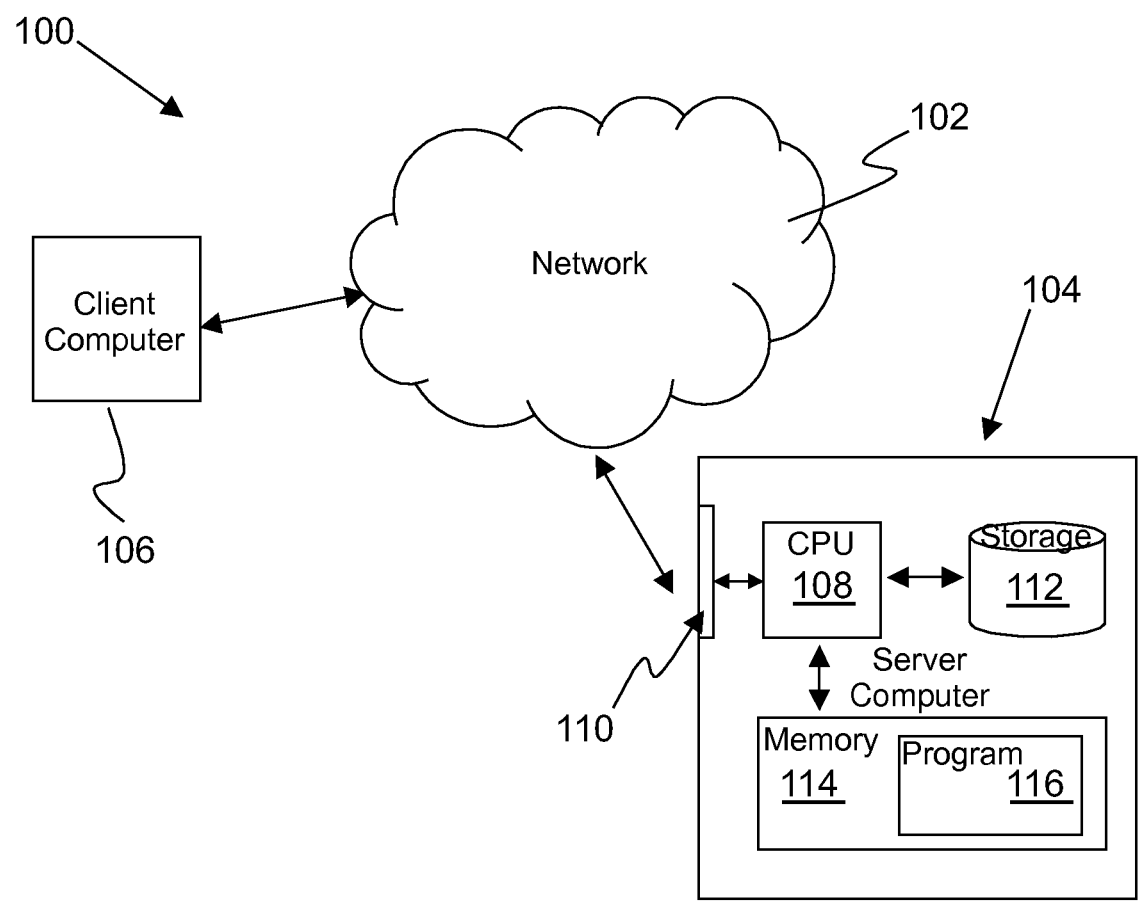
FIG. 1 is a block diagram of a system for measuring emotional response to sensory stimuli according to an embodiment of the invention.

With the foregoing in mind, FIG. 1 shows a block diagram 100 of a system for measuring emotional response to sensory stimuli according to an embodiment of the invention. The exemplary system 100 is based upon an online implementation, and accordingly various components of the system are interconnected via a network 102, which may be, for example, the Internet, a corporate intranet, a local area network (LAN), or any other suitable interconnecting network. An online system is desirable, because it enables the remote testing of a large number of individuals across multiple sites. However, it will be appreciated that the invention may also be implemented as a standalone system, for example as a dedicated software application executing on a single computer.

The exemplary system 100 further includes a server computer 104, and one or more client computers 106. In some embodiments, the system 100 is implemented using web-based technologies, such that the client computer 106 may be a suitable device capable of running standard web browser software, along with any required plug-in components. For example, the client computer 106 may be a desktop PC, a notebook PC, or a wireless handheld device, such as a PDA, mobile telephone, or the like.

The server 104 includes at least one microprocessor 108, which is interfaced with the network 102 via suitable network interface hardware 110. The server 104 further includes a high-capacity, non-volatile memory/storage device 112, such as one or more hard disk drives. The storage device 112 is used primarily to contain programs and data required for the operation of the server 104, and for the implementation and operation of various software components implementing an embodiment of the present invention. The means by which appropriate configuration and programming of the server computer 104 may be achieved (e.g. relevant programming languages, software development environments, and so forth) are well-known in the art, and accordingly will not be discussed in detail herein. However, exemplary technologies for implementation of certain components of the system 100 are mentioned, where relevant.

The storage device 112 may also be used to host one or more databases, or other files, maintaining results of emotional response measurements conducted on various test subjects. Alternatively, such databases may be remotely located, for example hosted by a database server and accessible via the network 102 and/or other interconnection.

The server computer 104 further includes an additional storage medium 114, typically being a suitable type of volatile memory, such as random access memory, for containing program instructions and transient data relating to the operation of the computer 104. The volatile memory device 114 contains a body of program instructions 116, embodying various software-implemented features of the present invention, as described in greater detail below with reference to FIGS. 2 to 8 of the accompanying drawings. In general, these features include data gathering, analysis and processing functions relevant to operation of the system 100, and particularly for presenting emotional response measurement content materials to users of remote computers 106, and for receiving user input in reply. Additionally, in this embodiment the executable instructions 116 include instructions implementing a web server application, to enable the facilities of the computer 104 to be accessed using conventional web browser technology as previously mentioned.

Embodiments of the present invention utilise metaphor-based animated and interactive visual scales for measuring the emotional responses of individuals. In the context of market research, it has been established that the impact of emotions on consumer decision-making processes cannot be ignored, because emotional reactions function as the gatekeeper for further cognitive and behavioural reactions. However, in order to effectively measure emotional response it is necessary to identify relevant emotions, appropriate corresponding metaphors, and to develop suitable animated visual scales based upon those metaphors, in order to measure the identified emotions.

Figure 2:
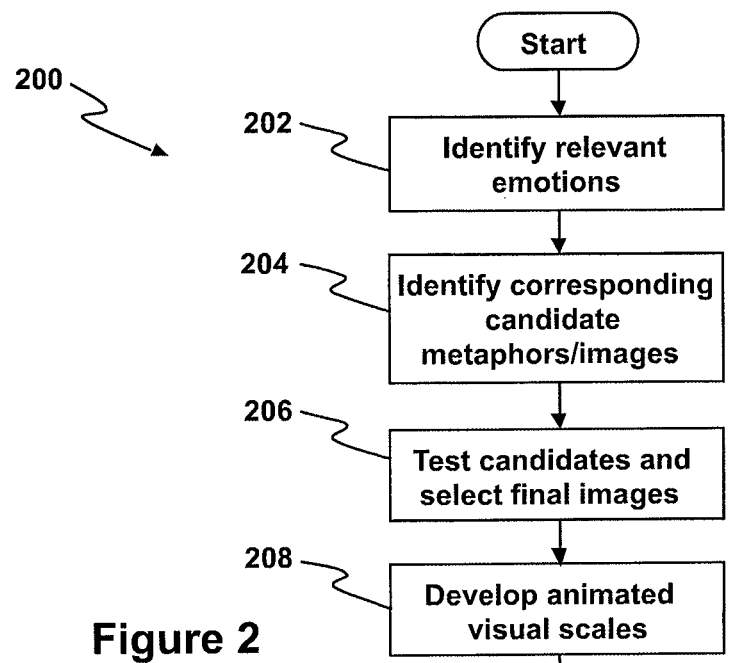
FIG. 2 is a flowchart representing a method of developing animated visual scales according to an embodiment of the invention.

FIG. 2 shows a flowchart 200 representing a method of developing animated visual scales for measurement of emotions, according to one embodiment of the invention. In particular, the method 200 comprises firstly identifying relevant emotions (step 202) and then identifying corresponding candidate metaphors and associated images (step 204). At step 206, the candidate metaphors/images are tested, to enable final selection of the most-effective candidates. Step 208 is the development of corresponding animated visual scales.

For purposes of the presently described embodiment, the step 202 of identifying relevant emotions has been based upon established research studies. Specifically, nine basic emotions have been identified, which are those most-frequently experienced across a wide range of consumption situations (Laros, F. J. M. and Steenkamp, J. B. E. M., 'Emotions in Consumer Behaviour: A Hierarchical Approach,' *Journal of Business Research*, Volume 58, 2005, pages 1437 to 1445; Richens, M. L., 'Measuring Emotions in the Consumption Experience,' *Journal of Consumer Research*, Volume 24 No. 2, 1997, pages 127 to 146). The nine identified emotions comprise four positive emotions, namely love, pride, contentment and happiness, four negative emotions, namely anger, sadness, shame and anxiety, and one neutral emotion, namely surprise.

The step 204 of identifying corresponding candidate metaphors and associated images was also based initially on a review of established research. In particular, Kovecses (2000) has described the possible primary metaphors that have been found to relate to primary emotions. For example, the emotional experience of love is often correlated with a physical experience of warmth, which comprises a metaphorical concept which for most people becomes embedded within the neural pathways of the brain at a very early stage in life. However, additional original research studies were also conducted in order to identify suitable candidate metaphors and images.

In particular, five focus groups were conducted, in which respondents were asked to describe the image that came to their minds in relation to a list of emotions, including the nine identified emotions listed above. From a total of approximately 50 participants, a list of approximately 250 images was generated. These were categorised according to the metaphorical domains associated with the images. It was found that similar underlying metaphorical themes were expressed across the images described by a range of different individuals for each targeted emotion. For example, the emotion of happiness was very commonly associated with 'being up', as well as with 'warm and sunny' images. These observations led to the selection of a final list of three candidate images per emotion.

Further original studies were then conducted (step 206) in order to test the candidate images (i.e. the three selected images per emotion) and select a single final image for each emotion. An initial pilot test was conducted, involving 31 participants, with the goals of finding the most effective test design, and also to obtain feedback on the test in relation to the difficulties encountered in completing the required tasks, and ease of understanding of the concepts behind the candidate images. The test methodology was based on the Implicit Association Test (IAT) described by Greenwald, McGhee and Schwartz (Greenwald, A. G., McGhee, D. E., and Schwartz, J. K. L., 'Measuring Individual Differences in Implicit Cognition: The Implicit Association Test,' *Journal of Personality and Social Psychology*, Volume 74, 1998, pages 1464 to 1480). The IAT is a computer-based technique that measures indirectly the strengths of associations among concepts, or pairs of concepts, in human memory. In particular, the visual images that best represent an emotion were tested, using the IAT technique, through the speed and accuracy with which participants were able to classify an image to a corresponding emotion. The test was conducted by programming the candidate images into the Inquisit™ software package from Millisecond Software™ (www.millisecond.com).

The most effective test design was then used in a further full study, in which the objective was to use a reaction time task (RTT) to identify the image, of the three candidates for each emotion, which would be most strongly associated with the targeted emotion. Each respondent in the study was required to complete the RTT, and self-report questions. An online study was conducted using a panel of 750 respondents in total, recruited by GMI (www.gmi-mr.com). Each panel member was sent a random selection of five Inquisit™ test links, with each RTT having a quota of 150 respondents out of the total panel of 750. The data gathered during the study was validated and cleaned according to procedures set out for the IAT, in particular by the deletion of trials with a reaction time of greater than 10,000 milliseconds, and the deletion of respondents for whom more than 10 percent of RTT trials exhibit a latency of less than 300 milliseconds.

The results were processed via an analysis of variance (ANOVA) model. In the event that the ANOVA results were significant between groups, a combination of visual concepts drawn from groups with the lowest latency and highest self-report scores were used for final image selection. In the event that ANOVA results were not significant between groups, it was concluded that the groups are equally associated (i.e. different images with a common emotion), based on the latency scores. In this case, the self-reporting results were analysed, in order to determine the mean frequency with which respondents associated specific candidate images with the target emotion. If the self-reporting mean frequencies were significant, then visual concepts based upon the self-reporting were used. On the other hand, if the self-reporting mean frequencies were not significant, then the image with the lowest latency was selected, on the basis that this is indicative of the strongest implicit (i.e. unconscious) association between the emotion and the candidate image.

Animated visual scales were then developed, using Adobe™ Flash™/Shockwave™, in order to facilitate web-based delivery of the interactive visual scales, i.e. within the system 100 shown in FIG. 1.

Figure 3:
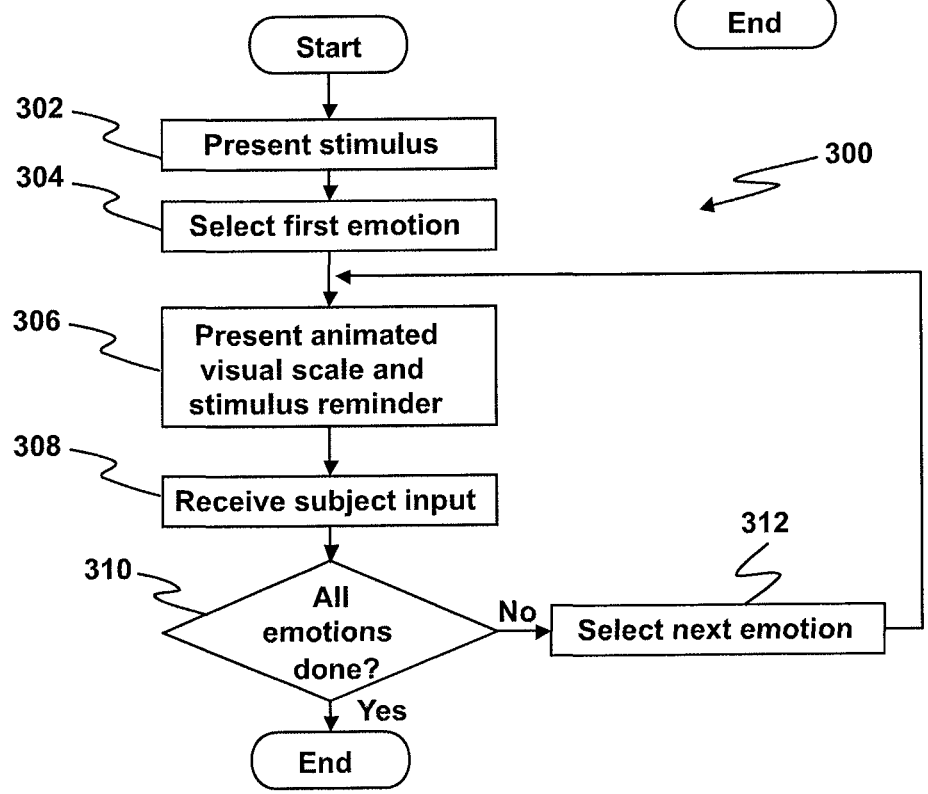
FIG. 3 is a flowchart representing a method of measuring emotional response to sensory stimuli corresponding with the system of FIG. 1.

A flowchart 300 representing a method of measuring emotional response to sensory stimuli is shown in FIG. 3. Specifically, according to this embodiment an audiovisual stimulus is first presented at step 302. This may be, for example, a series of images, and/or an advertising presentation, such as a 15-, 30- or 60-second commercial. The audiovisual stimulus may be streamed by the server 104 to a user device 106, via the Internet 102, or may be presented to the test subject via other means, such as within a viewing auditorium.

The measurement of emotional response is then conducted as follows. At step 304, the first emotion (of the nine emotions in this embodiment) is selected. The selection of the first emotion may be predetermined, or may be random. At step 306, the corresponding animated, interactive, visual scale is presented to the subject, along with a reminder of the audiovisual stimulus. The reminder may be, for example, a still image from a commercial, or a short repeated sequence. At step 308, the subject's input is received, by the subject manipulating the animated, interactive visual scale on the computing device 106, for example by clicking and dragging an appropriate image element using a mouse or other pointing device. The interactive scale may be provided, for example, by a browser executing on the user device 106 downloading the corresponding Adobe™ Flash™ application from the server 104 via the Internet 102, which then runs within a browser window using an Adobe™ Flash™ Player plug-in. At step 310 a check is performed to determine whether input has been received in respect of all nine emotions. If not, then at step 312 the next emotion is selected, e.g. either in sequence or at random. Steps 306 and 308 are repeated for the corresponding animated, interactive, visual scale. Once input has been received in relation to all nine emotions, the process 300 terminates.

Figure 4:
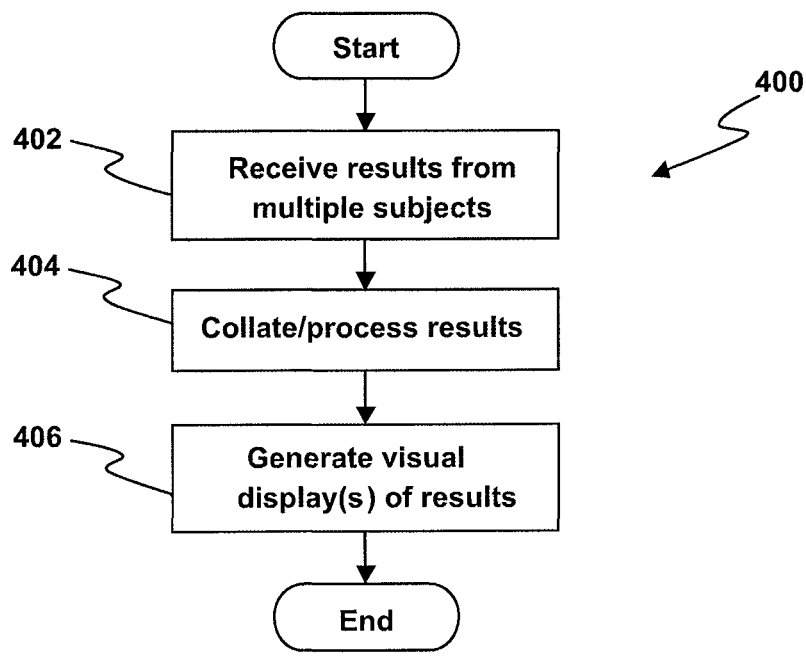
FIG. 4 is a flowchart representing a method of generating a visual display of results of measurement of emotional response of multiple subjects according to an embodiment of the invention.

FIG. 4 shows a flowchart 400 representing a method of generating a visual display of results of measurement of the emotional responses of multiple test subjects. In particular, it is highly desirable, according to some embodiments of the invention, to convert the results of measurement of emotional response into a form that is readily amenable to comprehension and interpretation. This may include, for example, the generation of suitable graphics, charts and/or numerical/statistical summaries. At step 402, the results of testing of multiple subjects (i.e. via the process 300) are received. At step 404 these results are collated, analysed and processed in order to generate suitable summaries and derived quantities. At step 406, one or more meaningful visual displays of results are generated. These may be, for example, presented on a computer screen for review and/or further manipulation, or may be output for printing and/or inclusion in written reports.

Figure 5:
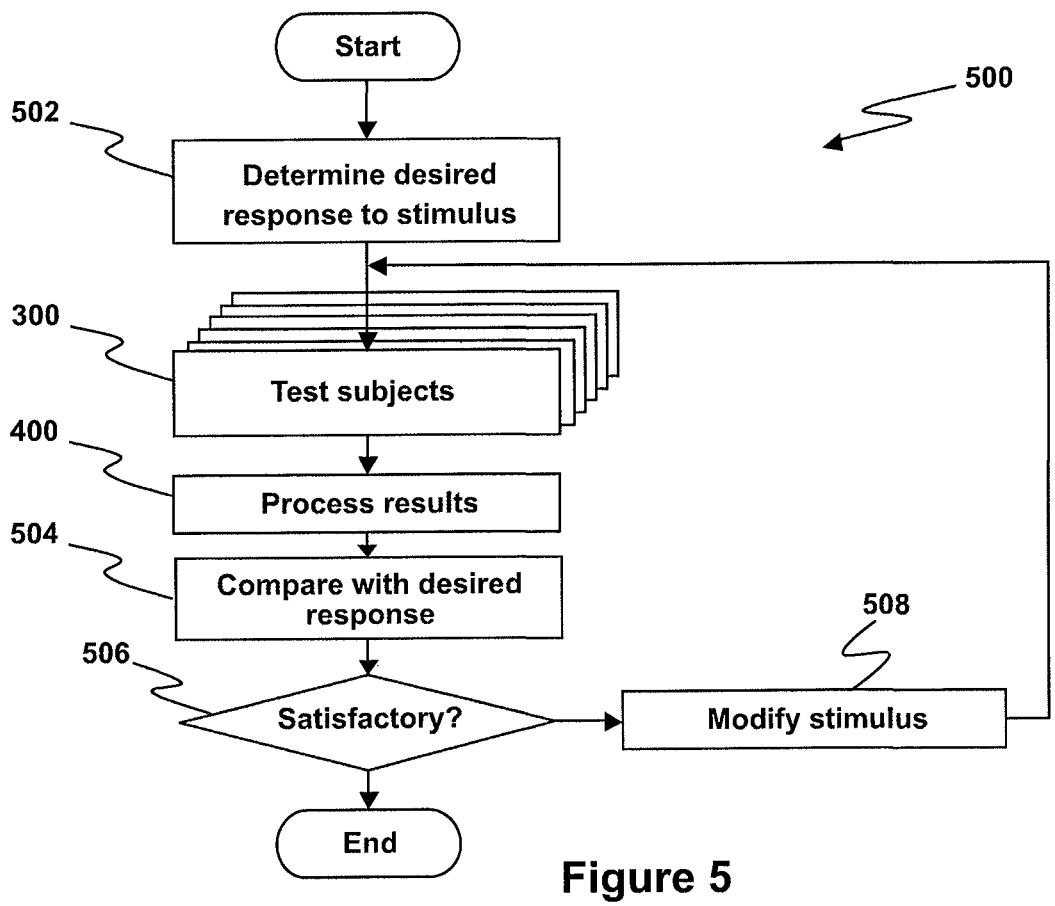
FIG. 5 is a flowchart representing a method of adapting a sensory stimulus to produce a desired emotional response according to an embodiment of the invention.

FIG. 5 is a flowchart 500 representing a method of adapting a sensory stimulus to produce a desired emotional response, according to one embodiment of the invention. In particular, in the field of marketing a vendor may wish to create particular emotional associations with a brand, for example through the form and/or content of relevant advertising presentations. At step 502, the desired response to the stimulus, e.g. an advertisement, is determined. Conveniently, the desired emotional response may be represented using similar visual display techniques to those generated from measurements of emotional response of test subjects, i.e. at step 406 of the method 400. This approach advantageously facilitates subsequent comparison between desired response and measured response.

A group of test subjects are then presented with the stimulus, and emotional response measured via the process 300. The resulting measurements are processed via the method 400, and then at step 504 the results of the measurements are compared with the desired response determined at step 502. As noted above, it may be particularly convenient to perform the comparison via visual means.

At step 506 a determination is made as to whether the comparison between the desired emotional response, and the actual measured emotional response, is satisfactory. If so, then the process 500 terminates. If not, then at step 508 the stimulus may be modified in an attempt to elicit an emotional response more closely correlated with the desired response. This may, for example, involve adaptations to the form and/or content of an advertising presentation. The testing 300, processing 400 and comparison 504 methods and steps are then repeated. In an alternative arrangement, a predetermined set of two or more audiovisual presentations may be provided in turn to each test subject, and emotional responses to each presentation measured. All responses may then be compared to the desired response (i.e. at step 504) to determine which presentation elicits a response most closely corresponding with the desired response. Depending upon the outcome, one or more further presentations may be developed in an effort to elicit a response more closely correlated with the desired response.

Figure 6:
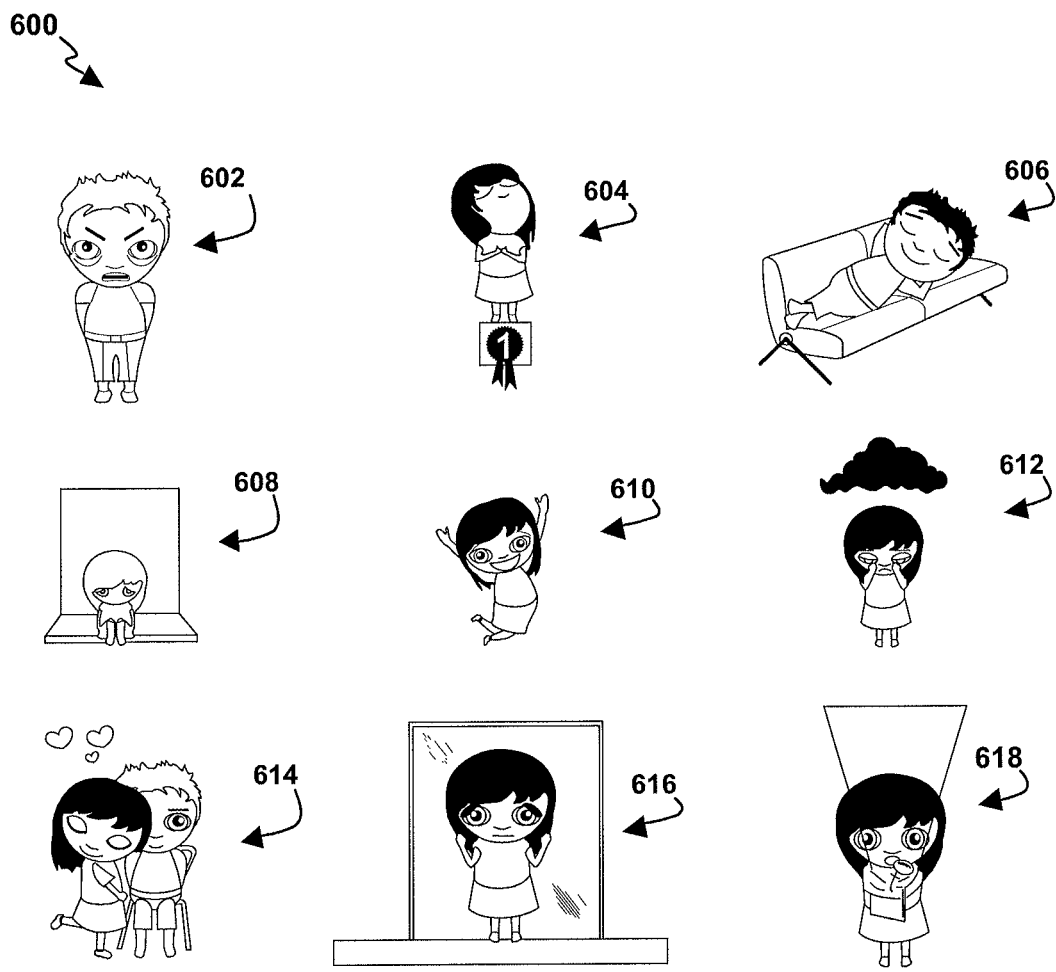
FIG. 6 shows images depicting selected visual metaphors according to an exemplary embodiment of the invention.
Figure 7A:
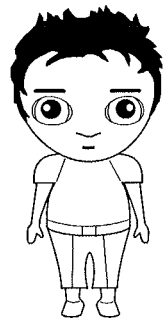
FIGS. 7(a), (b) and (c) are exemplary screen images from a metaphor-based emotional response test according to one embodiment of the invention.
Figure 7A:
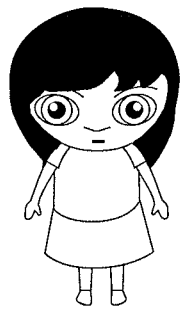
Figure 7A:
Figure 7A:
Figure 7A:
Figure 7A:
Figure 7A:
Figure 7B:
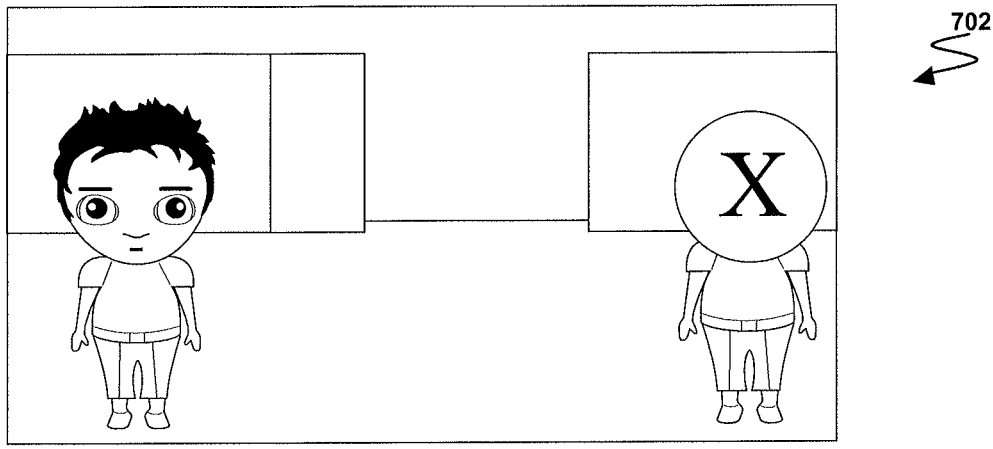
Figure 7B:
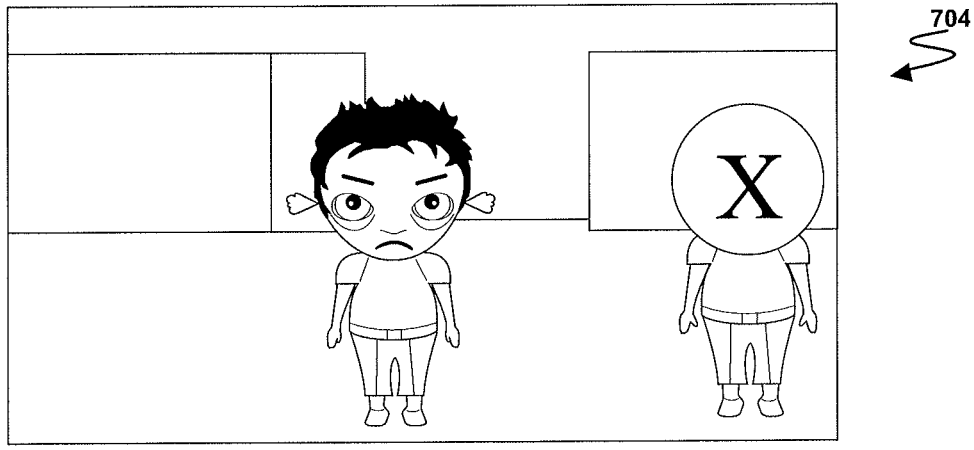
Figure 7B:
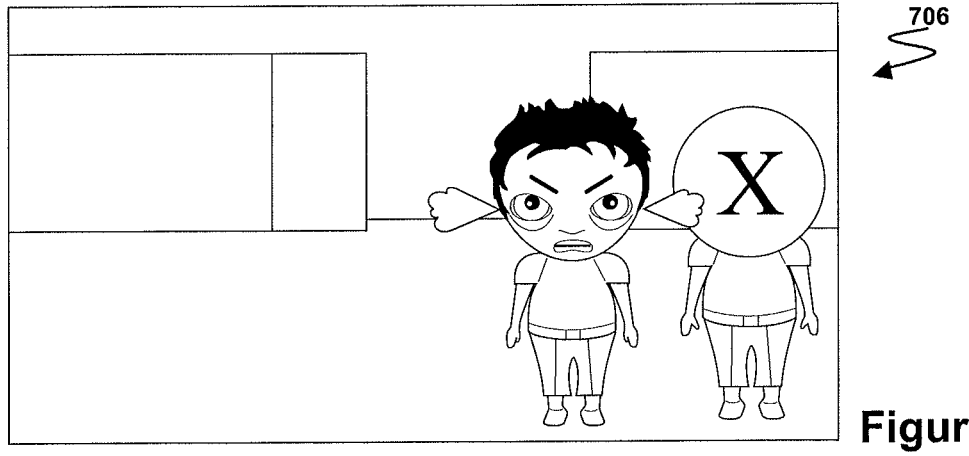
Figure 7C:
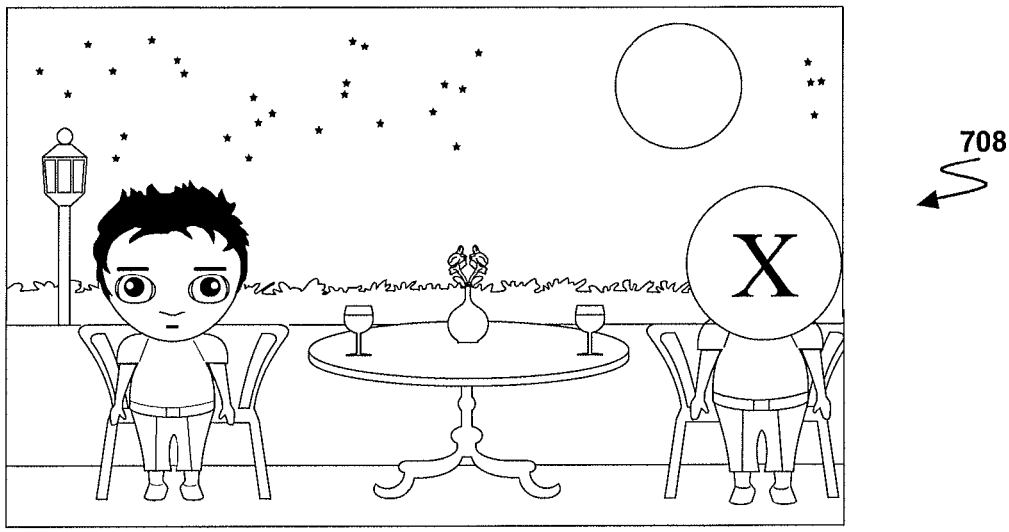
Figure 7C:
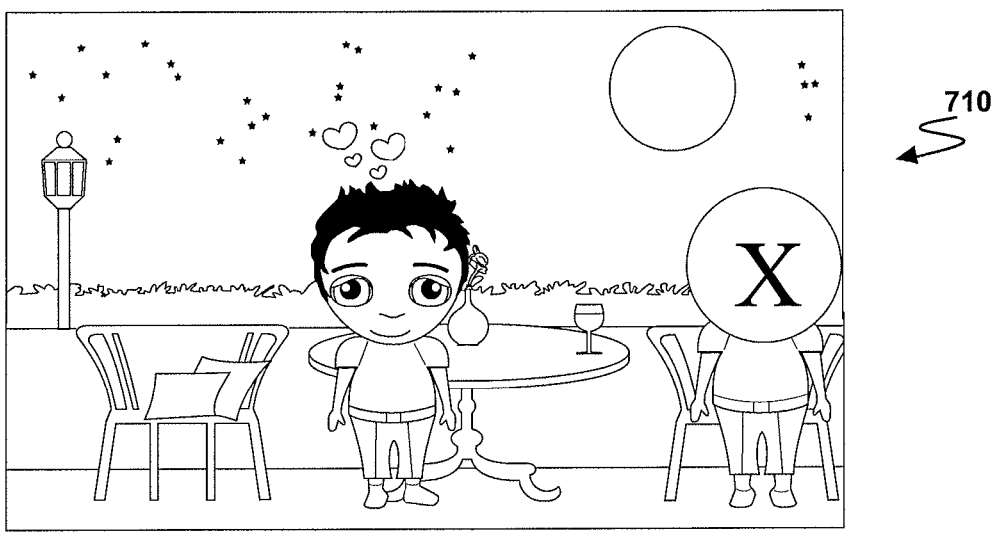
Figure 7C:
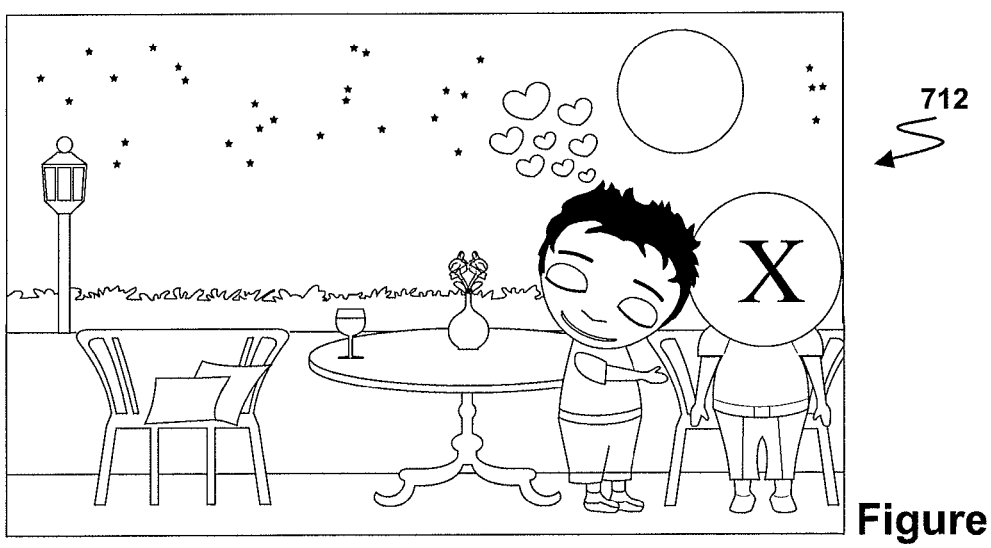
Figure 8A:
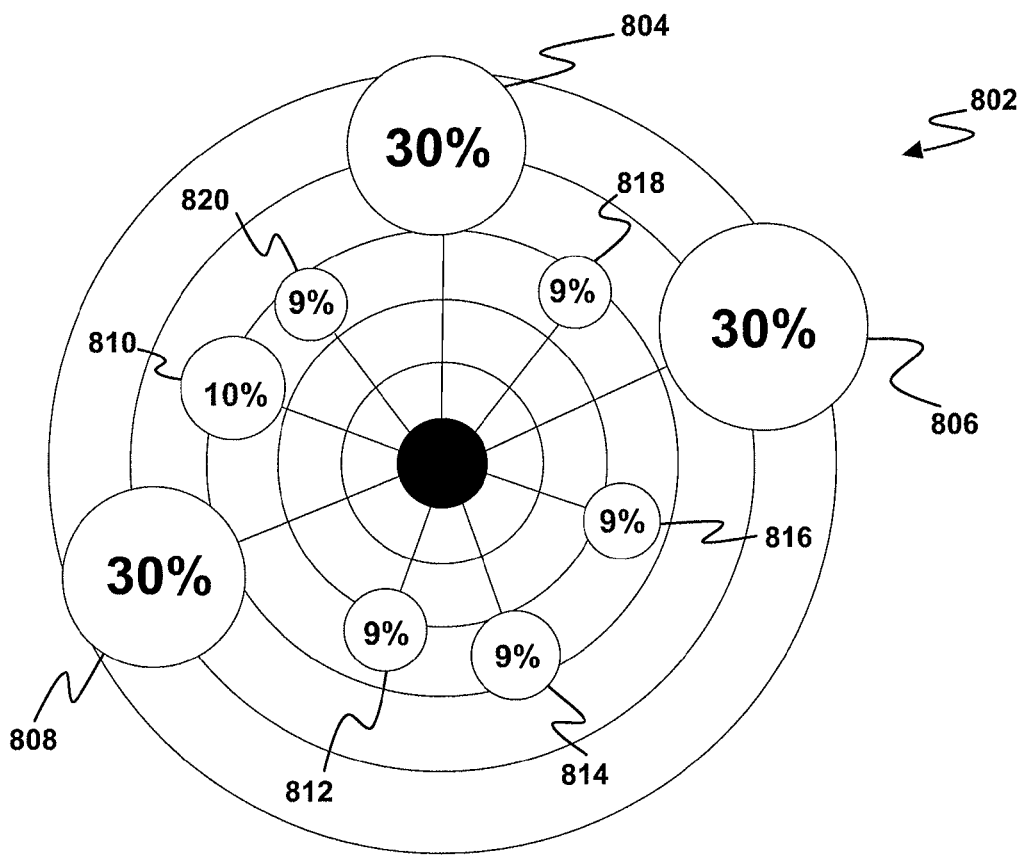
FIGS. 8(a), (b), and (c) are graphics illustrating a visual display of results according to one embodiment of the invention.
Figure 8A:
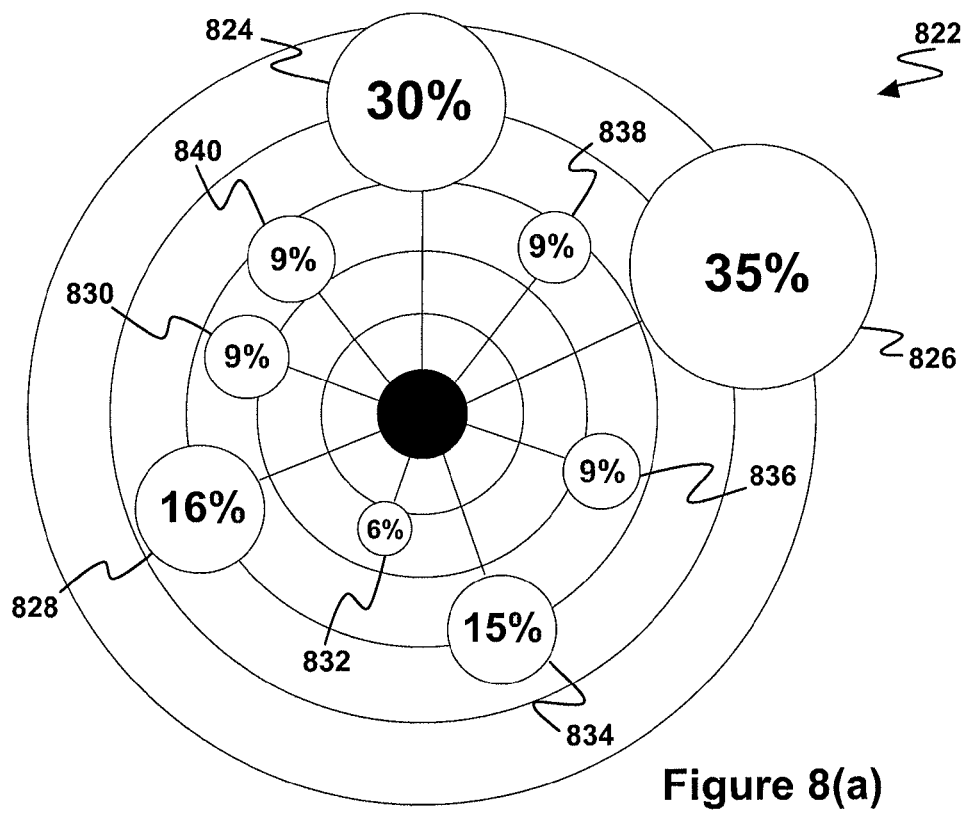
Figure 8B:
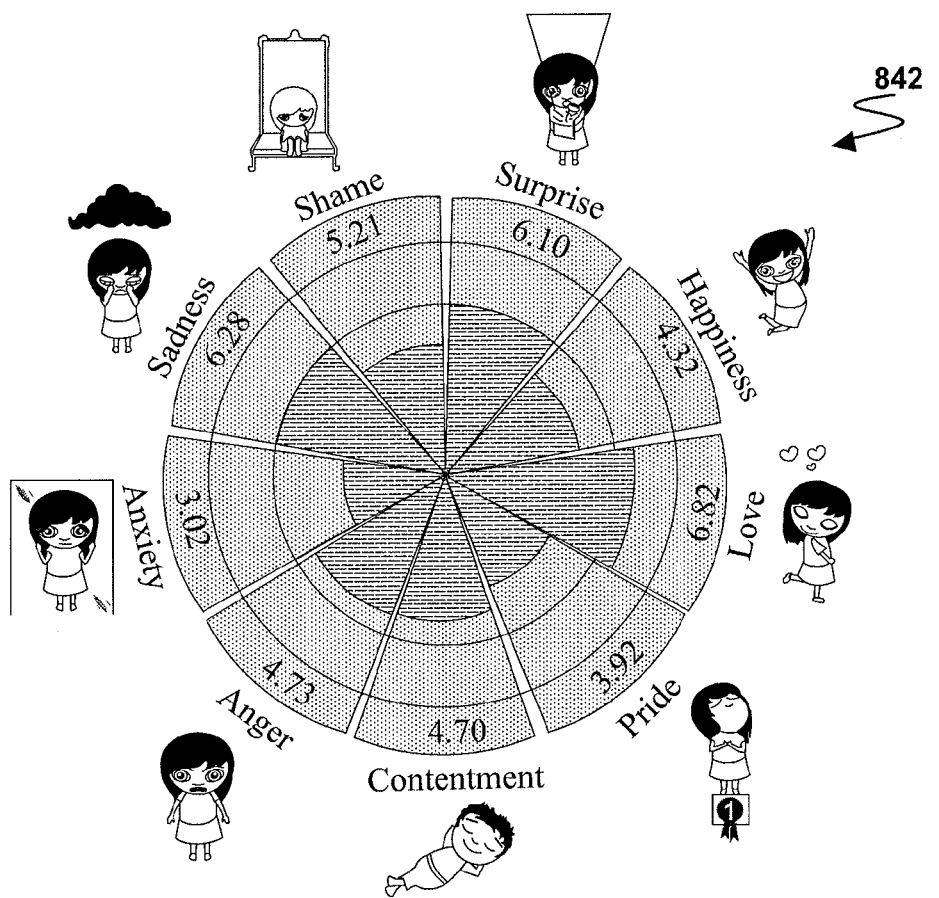
Figure 8B:
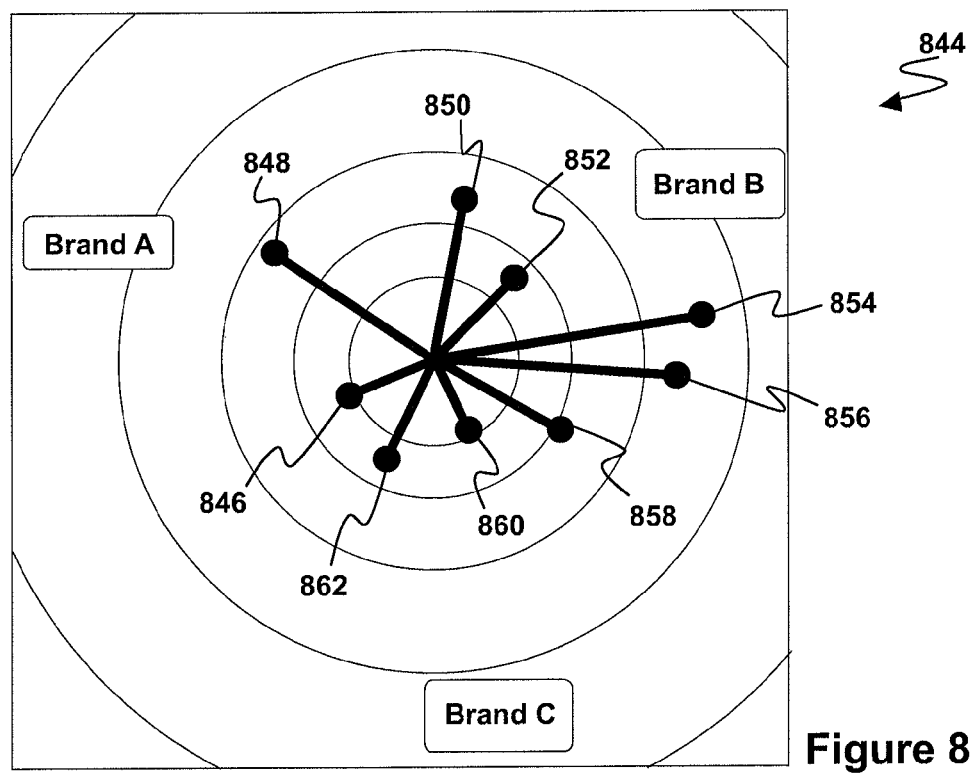
Figure 8C:
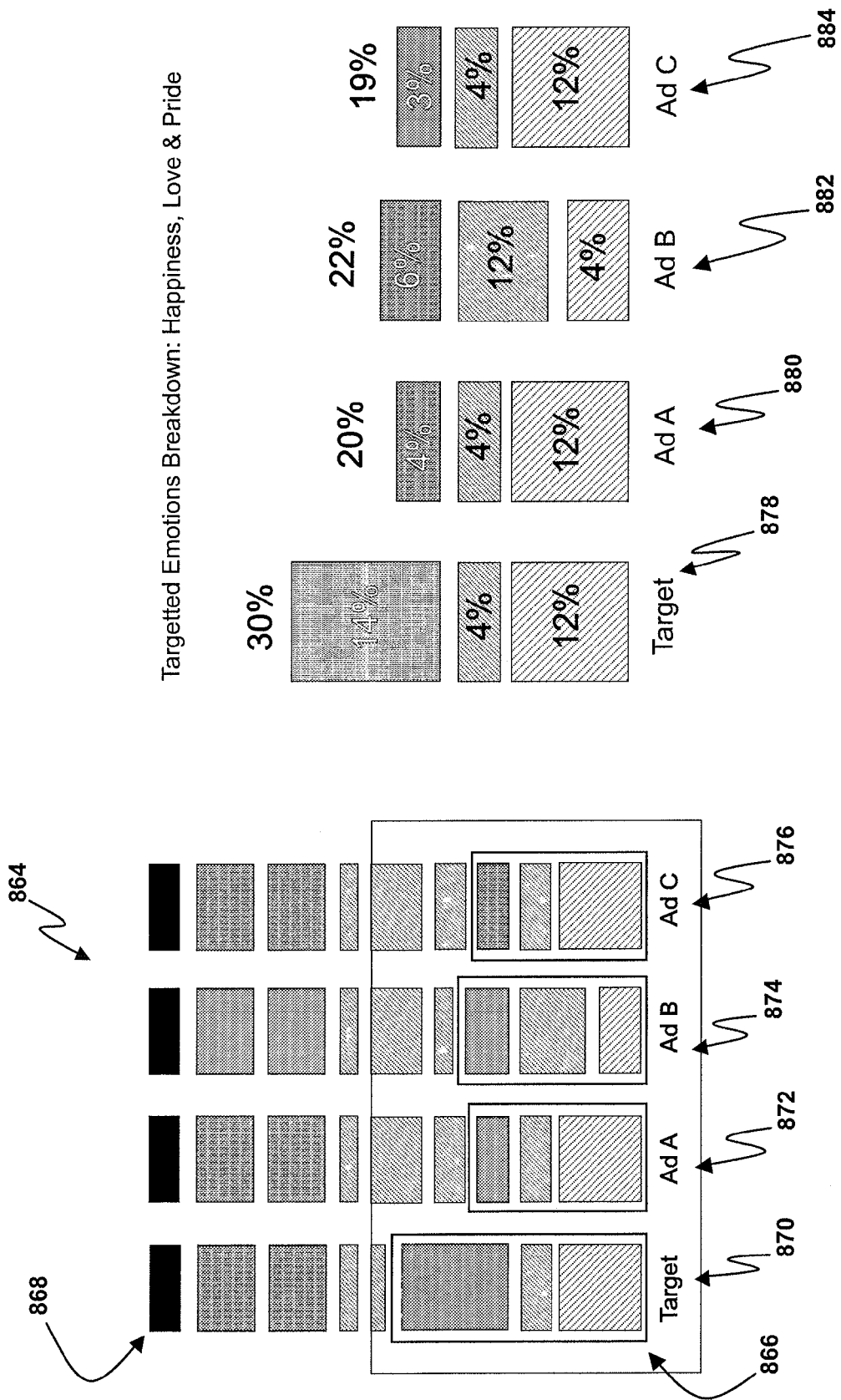

FIG. 6 shows a series of images 600 determined, in accordance with the study described previously, to provide the most suitable metaphorical representations of the nine emotions covered by this embodiment, i.e. these are the images selected at step 206 of the process 200. The nine selected images may be described as follows:

anger (602) is fire and/or heat;
pride (604) is superiority/elevation;
contentment (606) is a warm, pleasurable sensation;
shame (608) is insignificance or smallness;
happiness (610) is 'up' and off-the-ground;
sadness (612) is dark and down;
love (614) is a bond, and closeness;
anxiety (616) is an enclosing illness or natural force; and
surprise (618) is a bursting container.

The nine metaphorical images/emotions 600 were provided to a graphic animator to be transformed into a corresponding set of animated visual scales using Shockwave™/Flash™ technology. While the scales are entirely graphical in nature, and include no text or numeric indicators, in this embodiment each implements an 11 numeric point Likert-type scale. These scales allow for a measurement of intensity of emotion, and the result of a subject's interaction with each visual scale is a numerical result taking one of 11 possible values (e.g. 1 to 11, 0 to 10, −5 to +5, or equivalent). Importantly, therefore, the measurements of emotional response provided by embodiments of the present invention are quantitative in nature, and differentiate between specific emotions (i.e. nine different emotions, in the embodiment described herein).

FIG. 7 comprises a number of screenshots showing exemplary images from the visual scale testing software. FIG. 7(*a*) shows two introductory screens, the first of which (700) enables the subject to select a gender for a character representing them during the test, by clicking on either a male or female image. The subsequent screen 701 then allows the subject to select any one of a number of available characters, of the selected gender (in this case female) to represent them during the remainder of the test. These characters or 'avatars' may represent a number of different ethnicities and/or body types to enable the subject to select a representation with which they are able to closely identify. Advantageously, this may improve the subject's engagement with the test, resulting in input that is more closely representative of emotional response.

FIG. 7(*b*) shows three exemplary screenshots from the animated scale representing anger. The subject interacts with this scale by clicking on their avatar, and dragging the image to the left or right of the display, i.e. further away from, or closer to, the brand image, to select a position and representation that most closely matches their emotional response to the brand following exposure to the sensory stimulus. Image 702 reflects a low level of anger, towards the left of the scale. Image 704 represents a medium level of anger, towards the middle of the scale, indicated by the facial expression of the avatar, as well as a level of colouration of the face, and steam from the ears, correlating with the heat metaphor. Image 706 represents a high level of anger, at the right end of the scale, in which the heat metaphor is reflected in a higher level of colouration, and greater quantities of steam.

The sequence of images shown in FIG. 7(*c*) corresponds with the emotion of love, metaphorically represented by physical proximity and a 'bond'. Notably, the visual imagery includes romantic elements, including wine glasses and flowers, evoking the bond associated with romantic love. Image 708 reflects a low level of love, at the left end of the scale, in which the avatar is both physically and metaphorically distant from the brand image. Image 710 represents a medium level of love, towards the centre of the scale, in which the avatar is physically closer to the brand image, with the facial expression and four hearts above the avatar's head representing stronger feelings of romantic, love. Image 712 represents a high level of love, towards the right of the scale, in which the closeness has extended to physical contact, and blissful feelings of deep romantic love are reflected in the avatar's facial expression, and a greater number of hearts above the avatar's head.

Similar animated visual scales have been developed incorporating the remaining metaphorical images 600 shown in FIG. 6.

FIGS. 8(*a*), (*b*) and (*c*) illustrate various visual displays of results that may be generated by embodiments of the invention, i.e. at steps 406 and/or 504.

FIG. 8(*a*) shows two charts, referred to herein as 'molecule charts', representing one form of visual display of results. The charts depict the aggregated results of measuring the emotional response of multiple subjects to respective audiovisual representations comprising television commercials advertising low fares provided by a cut-price airline. The chart 802 depicts the response of the subjects to a first television commercial advertising low domestic fares. Each of the nine measured emotions is represented in the chart 802 by a disc, or 'atom' which, in one embodiment, is differentiated via colour with an appropriate key. The average emotional response measured for the test subjects in respect of each emotion is simultaneously represented by distance from the centre of the radial chart, size of the corresponding disc, and a percentage value appearing within the disc, wherein zero percent represents the lowest emotional response value (i.e. at the far left-hand extreme of the animated visual scales), and 100 percent represents the maximum emotional response value (i.e. at the extreme right-hand side of the animated visual scales).

In the chart 802 the strongest emotional responses are anger 804, contentment 806, and happiness 808. The strong anger response perhaps reflects the experience and/or perceptions of various test subjects in relation to cut-price airlines generally, and/or the subject cut-price airline in particular. Accordingly, this may be an area for, development of the brand image and/or product offering. The strong responses of happiness and contentment are presumably desirable reactions to the audiovisual presentation. Significantly lower emotional response has been recorded in relation to love 810, surprise 812, anxiety 814, shame 816, sadness 818, and pride 820. These are presumably emotions that are not strongly evoked by the audiovisual presentation, and/or by the brand, which is perhaps unsurprising in the case of a cut-price airline.

The further chart 822 reflects emotional responses to a second television commercial advertising low-price international fares. The discs again represent anger 824, contentment 826, happiness 828, love 830, surprise 832, anxiety 834, shame 836, sadness 838, and pride 840. Compared with the domestic fare advertisement, the presentation relating to international fares evokes lower levels of happiness, but slightly greater levels of contentment. Slightly greater levels of anxiety have been recorded, which may relate to issues with longer-distance travel and/or the particular destination. Slightly lower levels of surprise have also been recorded.

FIG. 8(*b*) depicts two further visual representations of the results of measurement of the emotions of multiple test subjects, in this case responsive to an audiovisual stimulus promoting a brand of disposable diapers. The first chart 842 is a radial 'matrix' depicting the strength of responses in relation to each emotion scale. The emotions are indicated by name, along with an image providing a reminder of the associated metaphorical scale. Additionally, the actual average response on the 11-step numerical scale is shown alongside each name and image. At the centre of the chart, this average response level is visually reinforced using a coloured wedge, the radial extent of which is proportional to the respective average response value. As will be appreciated, this form of presentation provides an easily assessed visual profile of the emotional spectrum associated with the advertised brand.

The second chart 844 in FIG. 8(*b*) is a radial 'map' that summarises the emotional differentiation between three different brands of disposable diapers. In this case, each of the radial bars represents the variance of subject responses between the three different brands. Accordingly, a longer bar reflects an emotion that is experienced to a substantially different degree in response to audiovisual stimuli associated with each brand. Conversely, shorter radial bars reflect emotions that are felt to similar degrees in relation to all three brands.

The emotions depicted in the chart 844 are anxiety 846, contentment 848, anger 850, love 852, sadness 854, shame 856, pride 858, happiness 860, and surprise 862. By way of example, the three brands elicit similar emotional responses in relation to happiness and anxiety, but show a wide variance in emotional responses in relation to sadness and shame. This latter may be reflective of strong brand differentiation in the marketplace, whereas uniformly low variance in response across all emotions may indicate that the respective brands are not strongly differentiated in the marketplace.

FIG. 8(*c*) illustrates one form of visual representation that may be useful in facilitating a comparison between a desired response and a measured response, i.e. at step 504. In the chart 862 the relative magnitude of each measured average response, in respect of all nine emotions, is represented by a corresponding block in a vertical bar. The nine emotions are colour-coded, and ordered from bottom 866 to top 868 of each bar as: happiness; love; pride; contentment; anger; sadness; shame; anxiety; and surprise. The left-most bar 870 represents a desired target response. The further three bars 872, 874, 876 represent actual measured average responses to three different advertisements comprising audiovisual presentations. A more-detailed breakdown of three targeted emotions, namely happiness, love and pride is represented by the further bar charts 878, 880, 882, 884. While none of the three presentations elicit precisely the desired emotional response, the first (880) is arguably the closest, in that it elicits both happiness and love in the desired proportions, although the level of pride is substantially lower than desired. Indeed, all three presentations (880, 882, 884) fail to elicit the desired levels of pride. Since pride is generally experienced as a sense of superiority, associated with perceived 'prestige' of a brand, it is likely that this is an area requiring further development by the brand owner.

Advantageously, embodiments of the present invention may be particularly effective in assisting marketers to develop strong communications strategies by virtue of the unique ability to target and measure individual specific emotions. Communication strategies should not be focused merely on building up emotions per se, or simply seeking the activation of consumers' emotions. Emotional hype will not necessarily translate to purchase intention, because individual consumers will still assess the purchase situation with both their cognitive and unconscious mind. It is therefore desirable that businesses should first aim to identify the rational drivers of brand choice. Subsequently, effective communication strategies will build emotional content and linkages upon the rational drivers that are relevant to the target market. Studies that have been conducted by the present applicant have demonstrated a high predictive power of rational drivers to market share, and it is therefore vital that these drivers of purchase be used as the foundations upon which emotional content is built.

For example, in one study conducted in relation to the offerings of a postal delivery service provider, the rational driver of purchase within the target market was found to be reliability. That is, consumers of delivery services are, unsurprisingly, concerned primarily with feeling confident that their articles will arrive at the intended destination. Perhaps less obviously, however, the underlying emotion behind this rational driver was found to be anxiety. In other words, consumers' desires for reliability stem from an underlying concern about the potential consequences of non-delivery, whether this be the mere inconvenience of lost items, or, in a work context, the potential impact of lost items upon a person's employment. The possibly counterintuitive consequence of these findings is that it is desirable for the advertising communications created by a delivery service provider to activate a certain level of anxiety within members of the target market. This effectively 'primes' consumers to be receptive to the service offering, and is thus more likely to translate to a purchase intention. As the foregoing illustrative examples demonstrate, embodiments of the present invention can be used to measure the specific effect of proposed communications on subjects' emotional responses in respect of anxiety, and to refine the communications in order to more effectively and reliably evoke the desired emotional responses.

In another study, an embodiment of the invention was used to measure emotional responses to different proposed advertising campaigns of a major national retirement investment fund operator. The three alternative proposed campaigns focused respectively upon low fees, fund performance, and size (i.e. national reach). One interesting result of this study, which the embodiment of the present invention was able to identify but which could not have been reliably detected using prior art methods, was the distinctly different emotional reactions of existing fund members, as compared with non-members, in relation to the 'size' campaign. In particular, fund members showed higher levels of anger in their emotional response than non-members, who showed greater levels of pride. This suggests that members did not respond positively to the 'size' campaign, perhaps due to a perception that large size is associated with impersonal service and/or a lack of exclusivity. Non-members, on the other hand, appeared to associate size with prestige or status, and thus perhaps felt a greater desire for 'belonging'.

Figure 9:
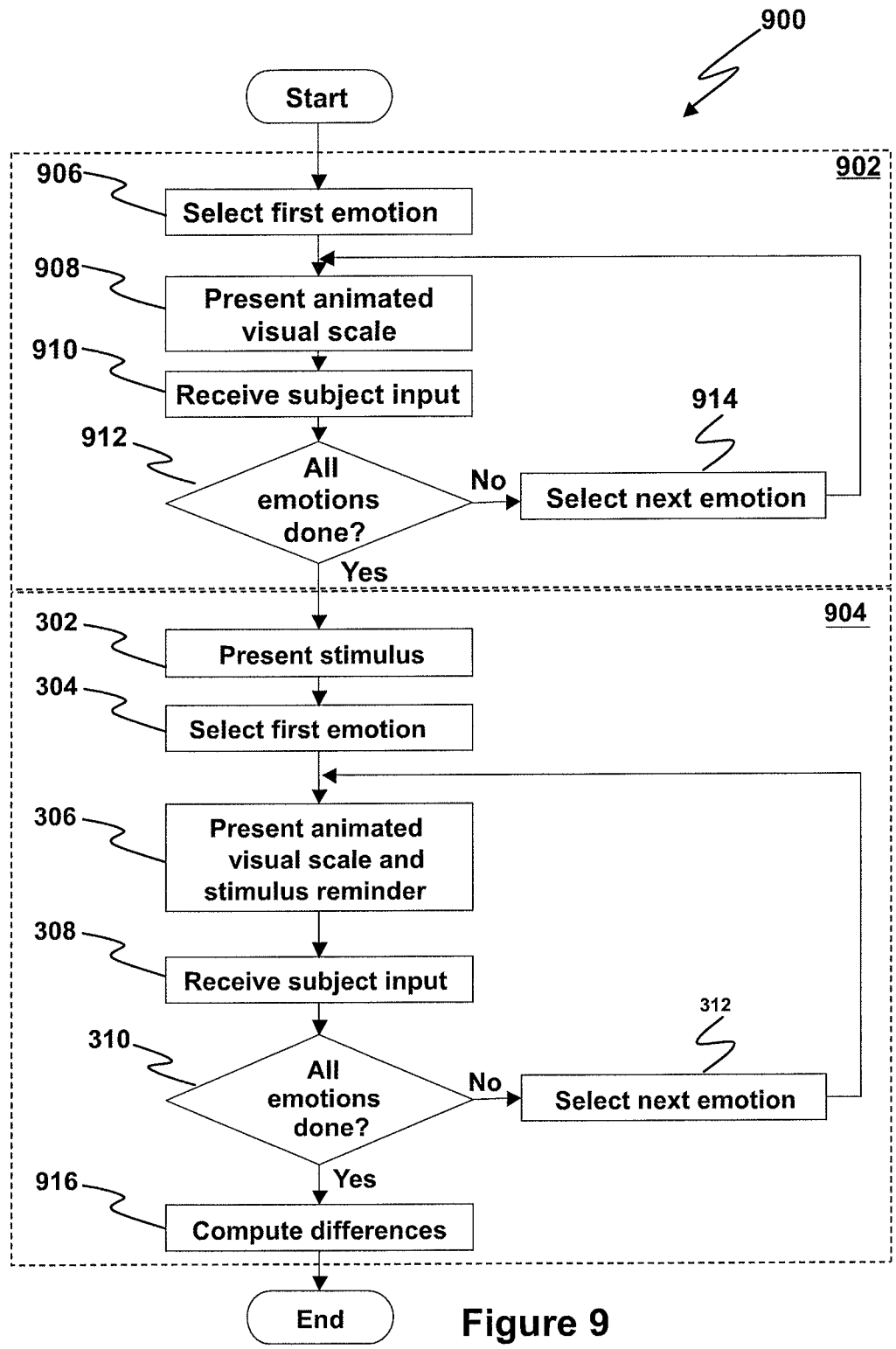
FIG. 9 is a flowchart representing a further embodiment of a method of measuring emotional response to sensory stimuli, which includes a calibration procedure.

Another embodiment of a method of measuring emotional response to sensory stimuli is shown in the flowchart 900 in FIG. 9. In the embodiment 900 the process is divided into two separate procedures. The first procedure 902 is a 'calibration' procedure, in which an initial emotional state of the test subject is measured. In the calibration procedure 902, no audiovisual stimulus is presented to the test subject. At step 906, the first emotion (of the nine emotions in one embodiment) is selected. As previously, the selection of the first emotion may be predetermined, or may be random. At step 908, the corresponding animated, interactive, visual scale is presented to the subject, but without any accompanying audiovisual stimulus reminder. At step 910, the subject's input is received, by the subject manipulating the animated, interactive visual scale on the computing device 106, for example by clicking and dragging an appropriate image element using a mouse or other pointing device. At step 912 a check is performed to determine whether input has been received in respect of all nine emotions. If not, then at step 914 the next emotion is selected, either in sequence or at random. Steps 908 and 910 are repeated for the corresponding animated, interactive, visual scale. Once input has been received in relation to all nine emotions, the process moves on to the second procedure of the method 900.

The main portion of the procedure 904 is identical with the method 300 shown in FIG. 3, in order to measure the subject's response to an audiovisual stimulus presented at step 302. In brief, a first emotion is selected at step 304, the corresponding scale presented to the subject at step 306, along with a reminder of the audiovisual stimulus, the subject input received at step 308, and the process repeated, via steps 310 and 312, until all nine emotions have been measured.

At step 916, the embodiment 900 again departs from the method of the embodiment 300. In particular, at step 916 a set of differences is computed between the responses of the subject in the second portion 904 of the process, and the corresponding responses during the first portion 902 of the process.

The differences computed at step 916 represent the change in the test subject's emotional state from that measured in the calibration stage 902 and following exposure to the audiovisual stimulus at step 302. In one embodiment, this change is computed simply by subtracting the scale values obtained during the first stage 902 from those obtained during the second stage 904. These difference values may therefore lie between, e.g., −10 and +10. However, since such dramatic changes in emotional state are uncommon, the resulting values will more typically lie within a smaller range, such as between −3 and +3. A difference value of zero, in this embodiment, represents the situation in which there is no change in the emotional state of the test subject, in respect of a particular measured emotion, following exposure to the audiovisual stimulus.

While subtraction is used in the embodiment described herein in order to determine the difference values, the scope of the invention is not so limited. For example, in alternative embodiments it may be desirable to divide the measured values after exposure to the audiovisual stimulus by the calibration values, to produce a metric in which a value greater than one represents a 'strengthening' of a particular emotion, while a value less than one represents a 'weakening' of the emotion. Still other metrics may be computed in alternative embodiments, such as a logarithm of a quotient of the measured values after and before presentation of the audiovisual stimulus.

It should be noted that, in this embodiment, 'surprise' is categorised as a positive affect emotion, rather than neutral, on the basis of further analysis of the impact of this emotion on consumer behaviour. In particular, Structural Equation Modelling (SEM) was employed in order to understand the underlying construct dimensions of the emotions. In general, SEM is a methodology that is well-known to persons skilled in the art of analysis of survey data, such as in the field of market research. The SEM methodology may be employed to estimate the unknown coefficients in a set of linear structural equations. Variables in the equation system are usually directly observed variables, such as the subjects' inputs via the interactive visual scales in response to the audiovisual stimuli, and unmeasured latent variables that are not observed but relate to observed variables, such as the subjects' underlying emotional responses. While SEM is a relatively complex form of analysis, its implementation is commonly aided by sophisticated software tools, such as the SPSS™ Amos™ SEM software, available from IBM Corporation.

By comparing different structural models, it was found that the emotions contentment, pride, love, happiness and surprise loaded together as one latent construct, while anger, sadness, anxiety and shame loaded together as a second latent construct. On the basis of this remodelling, therefore, 'surprise' has been categorized as a positive affect emotion in this embodiment, although it was originally anticipated that it might be a relatively neutral emotion. This demonstrates an advantageous feature of embodiments of the invention, namely the flexibility to adapt in response to changing hypotheses rather than being rigidly tied to fixed preconceptions.

Figure 10:
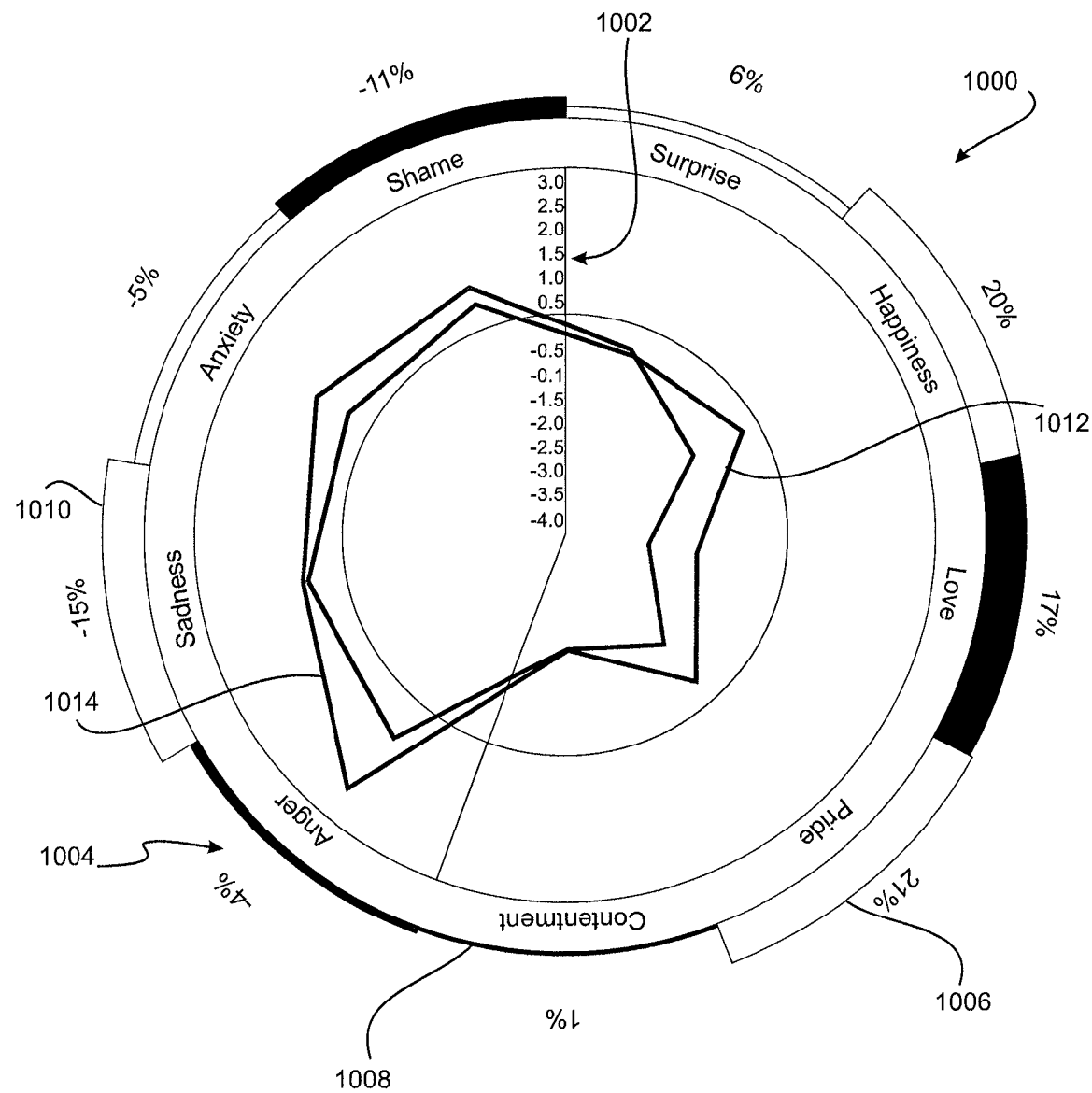
FIG. 10 is a chart comprising a visual representation of the results of measurement of the emotions of multiple test subjects using the method in the flowchart of FIG. 9.

FIG. 10 shows a chart 1000, which comprises a visual representation of the results of measurement of the emotions of multiple test subjects, using the method 900, responsive to an audiovisual stimulus promoting a particular retail banking institution. The chart 1000 has a scale 1002 ranging, as shown, from −4.0 to +3.0, representing the change in emotional state following exposure to the audiovisual stimulus.

Around the outer circumference of the chart 1000 is a 'ring' 1004 of bars representing the relative impacts of each one of the nine measured emotions on influencing consumer choice in relation to retail banking services. These impacts are represented as percentages, and corresponding thicknesses of the respective bars. Thus, for example, the bar 1006 represents the relative impact of pride, being 21%, the bar 1008 represents the relative impact of contentment, being 1%, and the bar 1010 represents the relative impact of sadness, being −15%.

The relative impacts (e.g. 1006, 1008, 1010) are obtained using the hierarchical Bayes modelling technique. Hierarchical Bayes modelling is well-established in statistical analysis, and will be familiar to persons skilled in the relevant arts. In brief, however, the hierarchical Bayes modelling technique considers each respondent to be a unique sample within a population, and applies information from other respondents to assist with modelling estimations, in order to obtain a different regression output for each respondent, as well as aggregate results for the overall product category (e.g. the retail banking services in the present example). This methodology enables the emotional drivers associated with consumer choice to be quantified and placed in a hierarchy.

In alternative embodiments, SEM may be employed to estimate the relative impacts of different emotions. However, hierarchical Bayes modelling has been found to provide improved flexibility and power over SEM, and to facilitate integration with analysis of rational drivers of behaviour, as discussed further below, with reference to FIG. 12.

Returning to FIG. 10, the relative impacts 1006, 1008, 1010 may be interpreted as follows. In this example, the positive emotion 'pride' (1006) has a relatively high positive impact of 21%. This means that pride is a relatively strong driver of consumer choice in relation to retail banking services. Accordingly, communications that tend to increase a sense of pride will have a relatively strong impact on consumer choice. By contrast, the emotion 'contentment' (1008) has a low relative impact of only 1%. Accordingly, communications that elicit feelings of contentment will nonetheless have relatively minimal impact on consumer choice. With regard to the motion 'sadness' (1010), this is a negative emotion and has a negative relative impact of −15%. This indicates that communications resulting in a reduction of levels of sadness are likely to have a relatively strong positive impact on consumer choice.

As will be appreciated, the use of graphical bars 1006, 1008, 1010 around the circumference 1004 of the chart 1000, in addition to the actual percentage values of the relative impacts, enables the emotions having the strongest relative impacts to be readily identified at a glance.

The test subjects in the example illustrated in the chart 1000 have been divided into two groups. In particular, the audiovisual stimulus presented to the test subjects was a television commercial for a particular retail banking institution. One set of results 1012 represents the emotional responses of customers of the advertised institution. The other set of results 1014 represents the responses of non-customers (i.e. customers of other banking institutions). The results show that non-customers generally experienced greater negative emotional responses, and particularly anger (towards their own financial institutions) than customers. Conversely, customers tended to experience greater positive emotional responses, such as pride and happiness, than non-customers, after viewing the television commercial.

Figure 11:
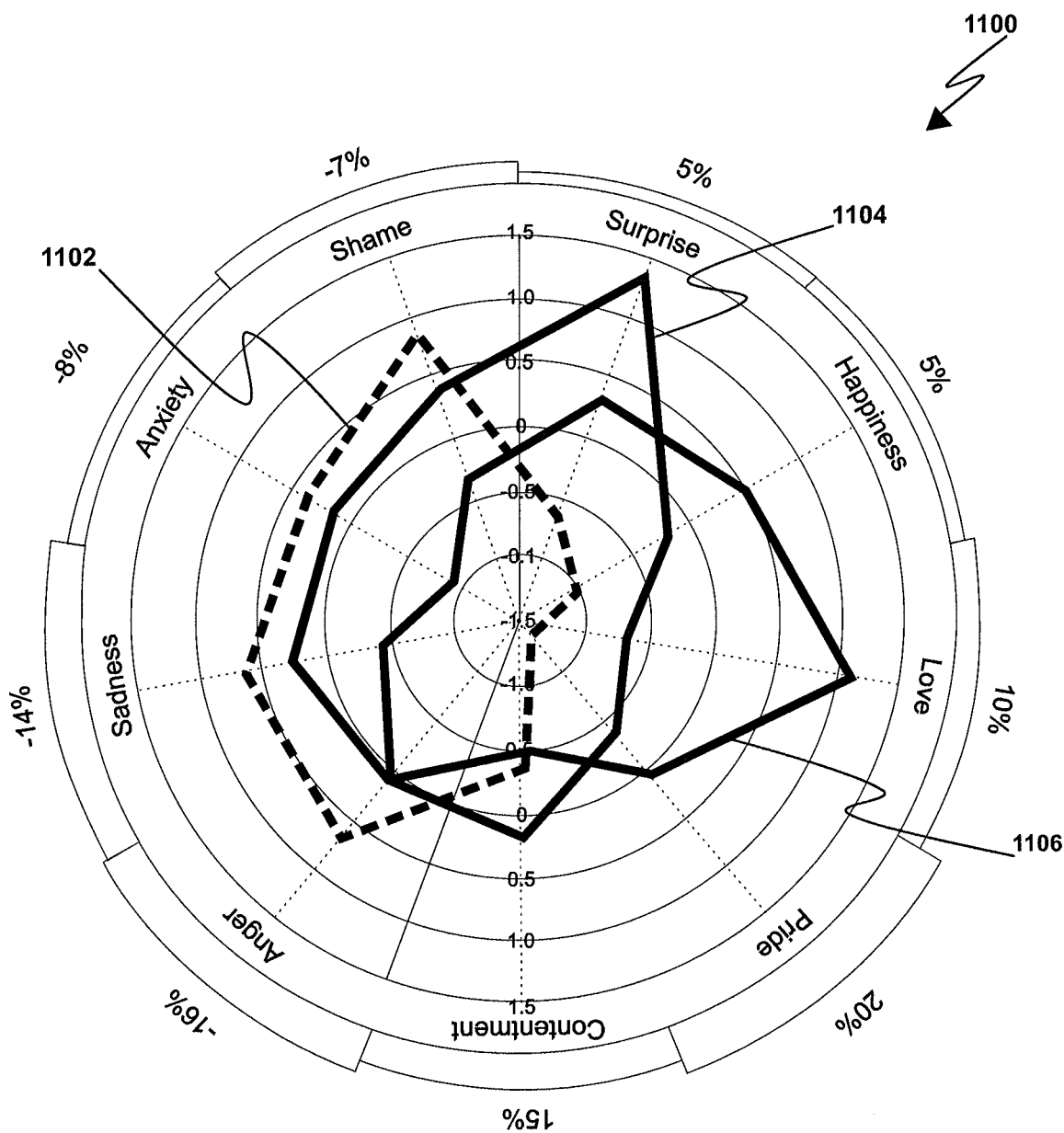
FIG. 11 shows a further chart comprising results of measurements performed in accordance with the method depicted in the flowchart of FIG. 9.

In yet another exemplary study, results of which are shown in the chart 1100 of FIG. 11, the method 900 was again applied to measure the emotional responses of a set of test subjects to a number of television commercials. The chart 1100 includes three sets of results. The first set of results 1102 represents the emotional response to the brand itself, i.e. prior to viewing any specific communications. The set of results 1104 represents the emotional responses of male viewers to the television commercial, while the results 1106 represent the emotional responses of female viewers. The responses of male and female viewers, in this particular case, are strikingly dissimilar. Overall, female viewers responded more favourably to each of the television commercials, with negative emotions being reduced and positive emotions increased to a greater extent than male viewers. Among male viewers, all television commercials generally reduced negative emotions, yet not all television commercials produced corresponding increases in positive emotions. Furthermore, the television commercials produced significantly different profiles in male and female viewers, highlighting the importance of television commercial selection to match program audience profiles.

In yet another embodiment, methods of measuring emotional response in accordance with the present invention are integrated with methods of analysis of the rational drivers of consumer choice, such as those disclosed in co-pending U.S. patent application Ser. No. 11/753,838, filed on 25 May 2007, the contents of which are hereby incorporated in their entirety herein, by reference. In particular, the hierarchical Bayes analysis, as discussed above, can be extended to include the division between rational and emotional drivers of consumer choice, at a higher level of the hierarchy. This method is then able, overall, firstly to derive the relative importance of rational and emotional components in predicting purchase choice, and, second, to produce the hierarchy of emotional drivers associated with purchase choice, as discussed above.

Figure 12:
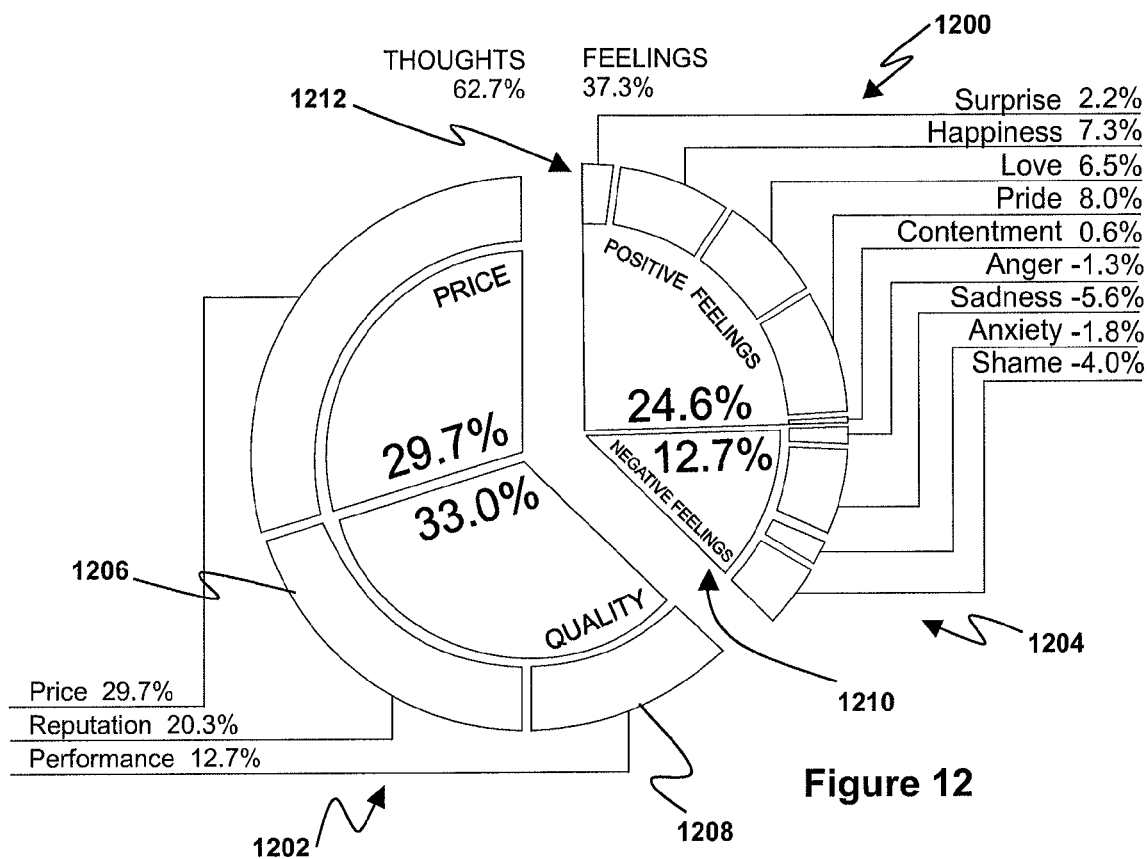
FIGS. 12 and 13 are charts illustrating the results of studies performed using an embodiment of the invention in which methods of analysis of rational drivers of consumer choice are integrated with methods of measuring emotional response.

A first chart 1200 illustrating results produced using this embodiment of the invention is shown in FIG. 12. In this example, the relative impact of rational drivers of choice (represented by the wedges 1202) was 62.7%, while the relative impact of emotional drivers, represented by the wedge 1204, was 37.3%. Within the hierarchy of rational drivers, quality and price were both of roughly equal importance. Performance contributed approximately one-third to the test subjects' perception of quality, while reputation contributed approximately two-thirds.

The hierarchy of emotional drivers is illustrated in the wedge 1204, and corresponds with the outer bars around the circumference 1004 in the exemplary chart 1000. In the chart 1200, the wedge 1204 representing emotional drivers is broken down into the relative impact of positive and negative emotions within the central portion 1210, and of the individual emotions around the outer circumference 1212. The chart 1200 therefore effectively shows the complete hierarchy of drivers of consumer choice at a glance.

Figure 13:
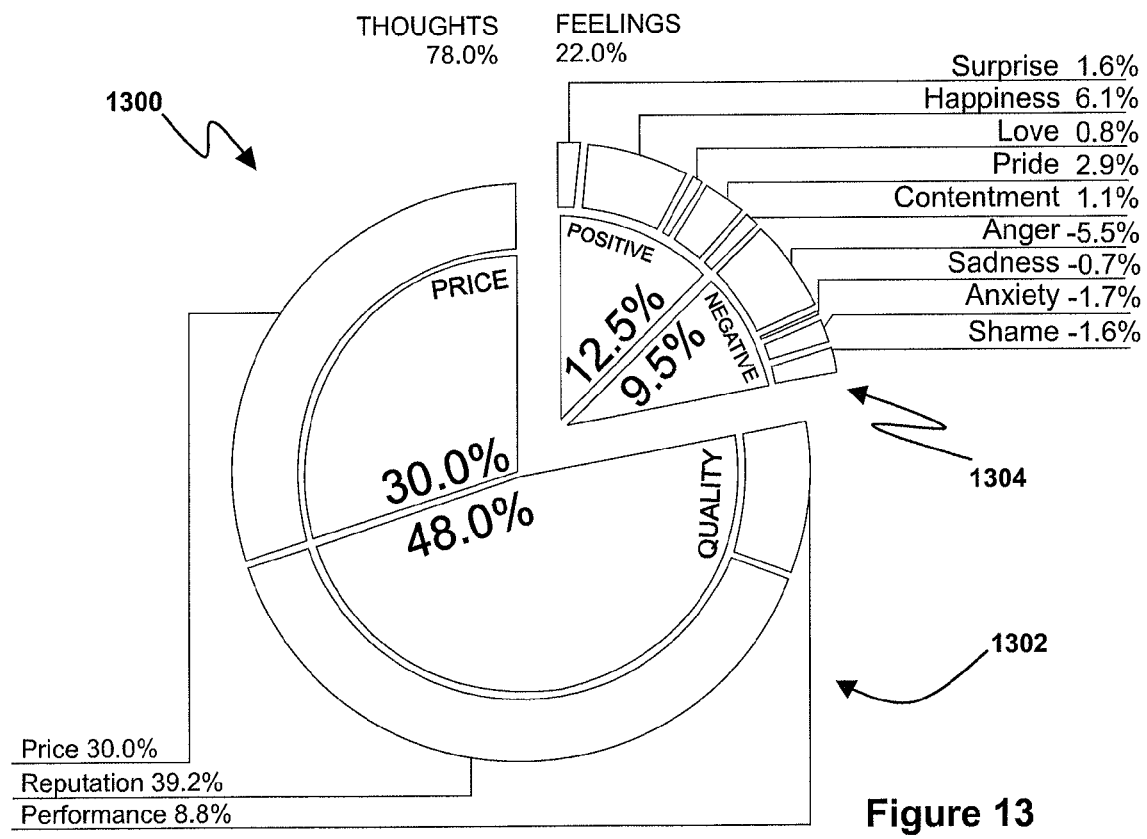

A chart 1300 illustrating the results of a further exemplary study is shown in FIG. 13. In this study, the rational drivers of consumer choice 1302 contribute 78%, while the emotional drivers 1304 contribute 22%.

A comparison of the two charts 1200, 1300 demonstrates how different communications, potentially directed to different audiences, may activate different profiles of rational drivers (i.e. cognitive engagement) and emotional drivers (i.e. feelings). Research has shown that rational drivers are more significant in retaining existing customers, while acquisition of customers (e.g. a consumer decision to switch from an existing provider to a competitor) is driven more strongly by an emotional response. Therefore, comparing the charts 1200, 1300 a response such as that shown in the chart 1200 is more desirable if the objective of a particular communication campaign is acquisition of new customers, while a response such as that shown in the chart 1300 is more desirable if the objective is retention of existing customers. Advantageously, methods embodying the invention as described herein, uniquely enable researchers and marketers to understand what proportion of a purchase decision is rational and what proportion is driven by emotion.

Figure 14:
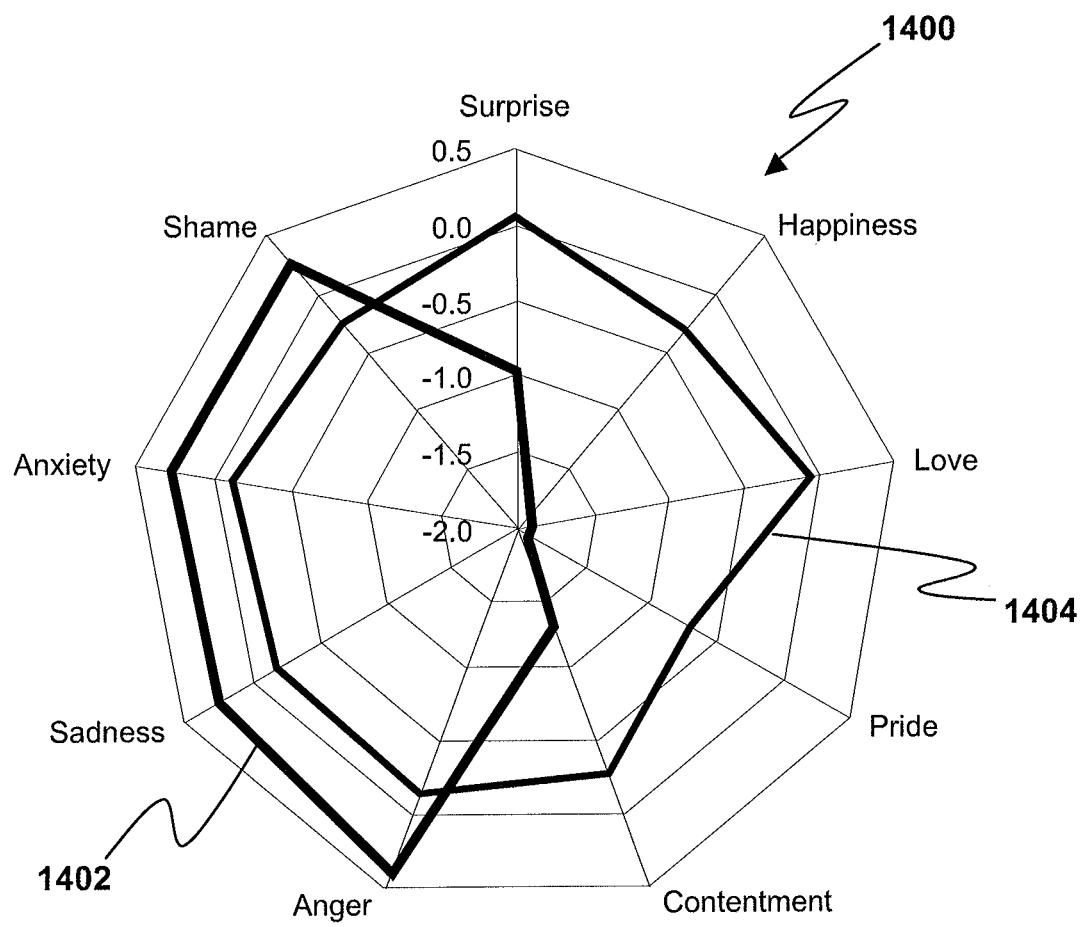
FIG. 14 is a chart showing the results of a further study using the method illustrated in the flowchart of FIG. 9, comparing emotional responses of test subjects to two different styles of communication.

Results of a further exemplary study are illustrated in the chart 1400 of FIG. 14. In this case, test subjects were exposed to two different television commercials, one of which (corresponding with results 1402) explicitly instructed viewers to 'be happy', while the other (corresponding with results 1404) communicated the same message implicitly, by showing scenes of happiness (e.g. a wedding). It is immediately clear that the explicit communication generally elicited negative emotional responses, while the implicit communication elicited more-positive responses.

The results of this exemplary study are congruent with the previously identified notion of unconscious environmental triggers for automatic processes in a consumer setting (see, e.g., Chartrand, T L, 'The Role of Conscious Awareness in Consumer Behaviour' *Journal of Consumer Psychology*, Volume 15, 2005, pages 203 to 210). Targeted emotions can be automatically activated in an implicit manner, and can guide subsequent behaviour and choices even outside of conscious awareness (see also Bargh, J A, 'Losing Consciousness: automatic influences on consumer judgement, behaviour, and motivation,' *Journal of Consumer Research*, Volume 29, 2002, pages 280 to 285). The results shown in the chart 1400 also support the established observations that people 'do not yearn for ads' nor do they like to be told to 'feel' a certain way. Hence, respondents apply a 'cynicism filter' when bombarded by advertising (see Tellis, G J, Advertising and Sales Promotion Strategy, Mass.: Addison Wesley, 1998).

Results of various case studies suggest that different emotions have different levels of diminishing marginal returns. That is, for each emotion there will be a point at which expending additional effort and expense to increase response will have a minimal further relative impact in driving consumer choice. Furthermore, different emotions do not share the same optimal levels. For example, emotions such as love and happiness have been found to have no real points of inflection, i.e. it is always beneficial to increase these emotional responses. However, for example, the emotion 'surprise' has been found to have an inflection point at around the values of three to four, on the scale of −10 to +10 utilised in the embodiment of the invention described above. This implies that it is necessary to be cautious about communications that evoke excessive levels of surprise, since inducing this emotion to a higher degree does not necessarily bring about an equivalent increase in brand choice. Similarly, it has been found that reducing anger to levels below about −4.5 achieves no practical additional benefit.

In summary, embodiments of the present invention provide an effective means, backed by advances in neuroscience and cognitive linguistics, for measuring the emotional response of individuals, and groups, to specific sensory stimuli, such as audiovisual presentations. An early application of the approach may lie in the fields of marketing and market research, where emotional responses are of interest due to the impact they have upon consumer behaviour. However, embodiments of the invention are not limited to this field of application, and may be employed in other circumstances in which it is desirable to measure the emotional response of individuals and/or groups. Suitable methodologies for developing animated visual scales for measuring emotional responses have been disclosed, and it is within the capability of persons skilled in the art to deploy these techniques for the development of further embodiments falling within the scope of the present invention. Accordingly, it will be understood that the scope of the invention is not limited to the particular embodiments or applications described herein, but rather is as defined by the claims appended hereto.

What is claimed is:

1. A computer-implemented method of measuring emotional response of at least one subject of a plurality of subjects to a specific sensory stimulus, comprising the steps of:
   establishing a plurality of basic emotions for measurement, including one or more positive affect emotions and one or more negative affect emotions;
   presenting the subject with the sensory stimulus;
   for each basic emotion, presenting the subject with a computer-generated display comprising interactive animated visual images representative of a metaphorical concept corresponding with the basic emotion;
   receiving input from the subject via a computer interface whereby the subject is enabled to adapt the animated visual images to accord with an emotional response to the sensory stimulus;
   a computer-implemented processor converting the received input to a corresponding quantitative emotional response value for each basic emotion;
   the computer-implemented processor performing a statistical analysis employing a latent variable mathematical model of the quantitative emotional response values of the plurality of subjects to identify one or more latent constructs, each of which comprises a subgroup of the plurality of basic emotions; and
   the computer-implemented processor generating a visual presentation comprising distinct representations of each one of the quantitative emotional response values for the plurality of basic emotions within the identified latent constructs, in which emotional responses of the plurality of subjects in respect of each one of the plurality of basic emotions within the identified latent constructs is visually distinguishable relative to all others of the plurality of basic emotions.

2. The method of claim 1 further comprising, prior to presenting the subject with the sensory stimulus, performing a calibration of an initial emotional state of the subject in respect of each basic emotion, and wherein the step of converting the received input to a corresponding quantitative emotional response value comprises the computer-implemented processor determining a difference value for each basic emotion based upon a change in emotional state of the subject from the initial emotional state.

3. The method of claim 2 wherein the calibration comprises steps of:
   for each basic emotion, presenting the subject with the computer-generated display comprising interactive animated visual images representative of a metaphorical concept corresponding with the basic emotion; and
   receiving input from the subject via the computer interface whereby the subject is enabled to adapt the animated visual images to accord with a current emotional state,
   wherein determining a difference value comprises subtracting an initial emotional state value from a corresponding value associated with the input received in response to the sensory stimulus.

4. The method of claim 1 wherein the plurality of basic emotions comprises emotions selected from the group comprising: love; pride; contentment; happiness; anger; sadness; shame; anxiety; and surprise.

5. The method of claim 1 wherein the animated visual images corresponding with each basic emotion are established by a method comprising the steps of:
   identifying a plurality of candidate metaphorical concepts and associated visual images;
   testing each candidate image with a panel of test subjects to determine a strength of association of the image with the basic emotion;
   selecting the candidate image with the strongest association with the basic emotion; and
   developing a computer-implemented sequence of animated interactive visual images representative of the metaphorical concept associated with the selected candidate image.

6. The method of claim 1 wherein, prior to or during the step of receiving input, the subject is presented with a reminder of the sensory stimulus.

7. The method of claim 6 wherein the sensory stimulus comprises an audiovisual presentation, and the reminder comprises a still image or a short sequence excerpted from the audiovisual presentation.

8. The method of claim 1 wherein the interactive animated visual images comprise an avatar representing the subject, which the subject manipulates via the computer interface to position the avatar closer to, or further from, a position representative of a strong emotional response.

9. The method of claim 8 wherein the quantitative emotional response value is a numerical value corresponding with the avatar position input by the subject via the computer interface on a scale from most distant to least distant from the position representative of the strong emotional response.

10. The method of claim 1 wherein the quantitative emotional response value takes one of a plurality of discrete values.

11. The method of claim 1 wherein the visual presentation comprises a numerical presentation.

12. The method of claim 1 wherein the visual presentation comprises a graphical presentation.

13. The method of claim 1 wherein the at least one subject comprises a plurality of subjects and the corresponding quantitative emotional value for each basic emotion is a single value derived from the combined input of all subjects.

14. The method of claim 13 wherein the step of converting the received input to a corresponding quantitative emotional response value comprises calculating an average response value for each basic emotion.

15. A method of comparing the emotional response of at least one subject of a plurality of subjects to one or more specific sensory stimuli with a desired emotional response, including the steps of:
(a) establishing a plurality of basic emotions for measurement, including one or more positive affect emotions and one or more negative affect emotions;
(b) determining desired relative emotional response values for each of the plurality of basic emotions;
(c) presenting the subject with a first sensory stimulus;
(d) for each basic emotion, presenting the subject with a computer-generated display comprising interactive animated visual images representative of metaphorical concept corresponding with the basic emotion;
(e) receiving input from the subject via a computer interface whereby the subject is enabled to adapt the animated visual images to accord with an emotional response to the sensory stimulus;
(f) a computer-implemented processor converting the received input to a corresponding quantitative emotional response value for each basic emotion;
(g) the computer-implemented processor performing a statistical analysis employing a latent variable mathematical model of the quantitative emotional response values of the plurality of subjects to identify one or more latent constructs, each of which comprises a subgroup of the plurality of basic emotions; and
(h) the computer-implemented processor generating a visual presentation comprising distinct comparative representations of the quantitative emotional response values of the plurality of subjects for each one of the plurality of basic emotions within the identified latent constructs, along with the corresponding desired emotional response values, whereby a correlation between relative emotional responses of the plurality of subjects in respect of each one of the plurality of basic emotions within the identified latent constructs and the corresponding desired emotional response is visually distinguishable.

16. The method of claim 15 wherein the at least one subject is further presented with one or more further sensory stimuli, and steps (d) to (h) are repeated for each said further sensory stimulus.

17. The method of claim 15 wherein a sensory stimulus is adaptively modified to improve the correlation between measured quantitative emotional response values and the predetermined desired emotional response values.

18. The method of claim 16 further comprising selecting one of the first and further sensory stimuli on the basis of correlation between measured quantitative emotional response values and the desired emotional response values.

19. A computer-implemented system for measuring the emotional response of at least one subject of a plurality of subjects to a specific sensory stimulus, the system comprising:
at least one microprocessor;
at least one memory device, operatively coupled to the microprocessor; and
at least one input/output peripheral interface, operatively coupled to the microprocessor,
wherein the memory device contains executable instruction code which, when executed by the microprocessor, causes the system to implement a method comprising the steps of:
for each one of a plurality of basic emotions, including one or more positive affect emotions and one or more negative affect emotions, presenting the subject via the peripheral interface with a computer-generated display comprising interactive animated visual images representative of a metaphorical concept corresponding with the basic emotion;
receiving input from the subject via the peripheral interface whereby the subject is enabled to adapt the animated visual images to accord with an emotional response to a sensory stimulus previously presented to the subject;
converting the received input to a corresponding quantitative emotional response value for each basic emotion;
performing a statistical analysis employing a latent variable mathematical model of the quantitative emotional response values of the plurality of subjects to identify one or more latent constructs, each of which comprises a subgroup of the plurality of basic emotions; and
generating a visual presentation comprising distinct representations of each one of the quantitative emotional response values for the plurality of basic emotions within the identified latent constructs, in which emotional responses of the plurality of subjects in respect of each one of the plurality of basic emotions within the identified latent constructs is visually distinguishable relative to all others of the plurality of basic emotions.

20. The method of claim 1 wherein the at least one subject comprises a plurality of subjects, the plurality of subjects being divided into at least a first subject group and a second subject group, and wherein:
the computer-implemented processor analysing the quantitative emotional response values comprises analysing the quantitative emotional response values to identify one or more latent constructs for each of the first subject group and the second subject group, each latent construct comprising a subgroup of the plurality of basic emotions; and
the computer-implemented processor generating a visual presentation comprises generating a separate visual presentation for each one of the first subject group and the second subject group, each visual presentation including distinct representations of each one of the corresponding quantitative emotional response values for the plurality of basic emotions within the corresponding identified latent constructs, wherein a comparative emotional response of the first subject group and the second subject group is presented in respect of each one of the plurality of basic emotions within the corresponding identified latent constructs.

21. The method of claim 1 wherein each interactive animated visual image is selected from a plurality of candidate images on the basis of tests conducted with a panel of test subjects to identify at least one candidate image resulting in low response latency which is indicative of a strong implicit association between the candidate image and the corresponding basic emotion.

22. The method of claim 1, further comprising:
the computer-implemented processor performing a statistical impact analysis to determine a relative impact value corresponding with each basic emotion, wherein each relative impact value comprises an estimate of influence of the corresponding basic emotion upon subject behavior; and
the computer-implemented processor generating the visual presentation including a representation of the relative impact value corresponding with each basic emotion.

23. The method of claim 22 wherein the statistical impact analysis comprises hierarchical Bayes modelling.

24. The system of claim 19 wherein the executable instruction code, when executed by the microprocessor, further causes the system to:
perform a statistical impact analysis to determine a relative impact value corresponding with each basic emotion, wherein each relative impact value comprises an estimate of influence of the corresponding basic emotion upon subject behavior; and
in generating the visual presentation, include a representation of the relative impact value corresponding with each basic emotion.

* * * * *

UNITED STATES PATENT AND TRADEMARK OFFICE
CERTIFICATE OF CORRECTION

PATENT NO. : 8,939,903 B2  
APPLICATION NO. : 13/162820  
DATED : January 27, 2015  
INVENTOR(S) : Kenneth George Roberts and Elaine Wong Page 1 of 1

It is certified that error appears in the above-identified patent and that said Letters Patent is hereby corrected as shown below:

Title Page, item (73),
At Assignee:
　"Forethough Pty Ltd"
should read:
　--Forethought Pty Ltd--

In the Specification,
At column 12, line 27:
　"feelings of romantic, love."
should read:
　--feelings of romantic love.--

At column 12, line 64:
　"be an area for, development"
should read:
　--be an area for development--

Signed and Sealed this  
Nineteenth Day of May, 2015

Michelle K. Lee  
*Director of the United States Patent and Trademark Office*